(12) United States Patent
Higuchi et al.

(10) Patent No.: US 11,844,609 B2
(45) Date of Patent: *Dec. 19, 2023

(54) FINGERPRINT CAPTURE SYSTEM, FINGERPRINT CAPTURE DEVICE, IMAGE PROCESSING APPARATUS, FINGERPRINT CAPTURE METHOD, AND STORAGE MEDIUM

(71) Applicant: NEC Corporation, Tokyo (JP)

(72) Inventors: Teruyuki Higuchi, Tokyo (JP); Yoshinori Koda, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,215

(22) Filed: Oct. 5, 2022

(65) Prior Publication Data

US 2023/0024027 A1    Jan. 26, 2023

Related U.S. Application Data

(63) Continuation of application No. 17/183,967, filed on Feb. 24, 2021, now Pat. No. 11,501,422, which is a
(Continued)

(30) Foreign Application Priority Data

Sep. 18, 2015    (JP) .................. 2015-186010

(51) Int. Cl.
*G06V 40/00* (2022.01)
*A61B 5/1172* (2016.01)
(Continued)

(52) U.S. Cl.
CPC .......... *A61B 5/1172* (2013.01); *A61B 5/7221* (2013.01); *G06T 1/00* (2013.01);
(Continued)

(58) Field of Classification Search
CPC .................. G06T 7/0002; G06T 1/00; G06T 2207/30168; A61B 5/1172; A61B 5/7221;
(Continued)

(56) References Cited

U.S. PATENT DOCUMENTS

| | | | |
|---|---|---|---|
| 5,446,934 A | 9/1995 | Frazier | A61G 11/00 5/421 |
| 6,185,319 B1 | 2/2001 | Fujiwara | |

(Continued)

FOREIGN PATENT DOCUMENTS

| | | |
|---|---|---|
| JP | 1-223576 A | 9/1989 |
| JP | 10-171968 A | 6/1998 |

(Continued)

OTHER PUBLICATIONS

U.S. Office Action for U.S. Appl. No. 18/075,783 dated Feb. 16, 2023.
(Continued)

*Primary Examiner* — Frank F Huang
(74) *Attorney, Agent, or Firm* — Sughrue Mion, PLLC

(57) ABSTRACT

A fingerprint capture system, a fingerprint capture device, an image processing apparatus, a fingerprint capture method, and a storage medium that can acquire a high quality fingerprint image are provided. A disclosed example includes: a capture unit that captures a fingerprint; an image processing unit that processes a transferred fingerprint image captured by the capture unit; a display unit on which the fingerprint image transferred to the image processing unit is displayed; a recording unit where the fingerprint image transferred to the image processing unit is recorded by the image processing unit; and an instruction unit that inputs, in the image processing unit, a record instruction that instructs the image processing unit to record the fingerprint image in the recording unit. The image processing unit records, in the
(Continued)

recording unit, the fingerprint image displayed on the display unit at the time the record instruction is input by the instruction unit.

8 Claims, 13 Drawing Sheets

Related U.S. Application Data continuation of application No. 15/760,862, filed as application No. PCT/JP2016/004226 on Sep. 16, 2016, now Pat. No. 10,984,514.

(51) Int. Cl.
  *G06T 1/00* (2006.01)
  *A61B 5/00* (2006.01)
  *H04N 23/53* (2023.01)
  *G06V 40/13* (2022.01)
  *G06T 7/00* (2017.01)

(52) U.S. Cl.
  CPC ............ *G06T 7/0002* (2013.01); *G06V 40/13* (2022.01); *H04N 23/53* (2023.01); *A61B 2503/04* (2013.01); *A61B 2503/06* (2013.01); *A61B 2576/02* (2013.01); *G06T 2207/30168* (2013.01)

(58) Field of Classification Search
  CPC ............ A61B 2503/04; A61B 2503/06; A61B 2576/02; G06V 40/13; H04N 23/53
  See application file for complete search history.

(56) References Cited

U.S. PATENT DOCUMENTS

| | | | |
|---|---|---|---|
| 6,469,166 B2 | 10/2002 | Fujiwara | |
| 6,671,392 B1 | 12/2003 | Shigematsu | G06K 9/00006 382/124 |
| 6,744,910 B1 | 6/2004 | McClurg et al. | |
| 6,871,010 B1 | 3/2005 | Taguchi et al. | |
| 6,886,104 B1 | 4/2005 | Mcclurg et al. | |
| 6,927,844 B2 | 8/2005 | Higuchi et al. | |
| 8,098,297 B2 | 1/2012 | Crisan et al. | |
| 8,846,985 B2 | 9/2014 | Inque et al. | |
| 2006/0018519 A1* | 1/2006 | Siegel | G06V 40/10 382/116 |
| 2007/0253605 A1* | 11/2007 | Maurer | G06V 40/1359 382/124 |
| 2008/0065468 A1 | 3/2008 | Berg et al. | G06Q 30/02 705/7.32 |
| 2011/0311111 A1 | 12/2011 | Allburn | G06K 9/00013 382/115 |
| 2013/0165809 A1 | 6/2013 | Abir | A61B 5/1135 600/534 |
| 2014/0198203 A1 | 7/2014 | Vardi | G08B 21/20 348/135 |
| 2014/0212008 A1 | 7/2014 | Hatcher, II et al. | |
| 2015/0036898 A1* | 2/2015 | Cohen | G06V 40/13 382/126 |
| 2015/0347725 A1* | 12/2015 | Ben Ari | G06F 21/31 726/19 |
| 2016/0210493 A1 | 7/2016 | Walch | G06K 9/001 |
| 2018/0005005 A1 | 1/2018 | He et al. | G06F 3/0418 |

FOREIGN PATENT DOCUMENTS

| | | |
|---|---|---|
| JP | 2000-222556 A | 8/2000 |
| JP | 2000-266162 A | 9/2000 |
| JP | 2002-159092 A | 5/2002 |
| JP | 2003-524224 A | 8/2003 |
| JP | 3751872 A | 3/2006 |
| JP | 2006-94059 A | 4/2006 |
| JP | 2006-113772 A | 4/2006 |
| JP | 2013-242914 A | 12/2013 |
| JP | 2014-146275 A | 8/2014 |
| WO | 2007/105768 A1 | 9/2007 |
| WO | 2011/070880 A1 | 6/2011 |

OTHER PUBLICATIONS

Japanese Office Action for JP Application No. 2021-113904 dated Jul. 12, 2022 with English Translation.
International Search Report for PCT/JP2016/004226, dated Dec. 13, 2016 (PCT/ISA/210).
Communication dated Jul. 9, 2019 from Japanese Patent Office in counterpart JP Application No. 2017-540511.
Office Action for U.S. Appl. No. 16/131,817 dated Mar. 9, 2020.
Notice of Allowance for U.S. Appl. No. 16/131,756 dated Feb. 24, 2020.
Extended European Search Report dated Apr. 10, 2019 issued by the European Patent Office in counterpart application No. 16845964.2.
Office Action dated Dec. 15, 2020 in Japanese Application No. 2019-206622.

\* cited by examiner

FINGERPRINT CAPTURE SYSTEM, FINGERPRINT CAPTURE DEVICE, IMAGE PROCESSING APPARATUS, FINGERPRINT CAPTURE METHOD, AND STORAGE MEDIUM

CROSS REFERENCE TO RELATED APPLICATIONS

The present application is a continuation application of U.S. patent application Ser. No. 17/183,967 filed on Feb. 24, 2021, which is a continuation application of U.S. patent application Ser. No. 15/760,862 filed on Mar. 16, 2018, which is issued as U.S. Pat. No. 10,984,514, which is a National Stage Entry of international application No. PCT/JP2016/004226 filed on Sep. 16, 2016, which claims the benefit of priority from Japanese Patent Application No. 2015-186010 filed on Sep. 18, 2015, the disclosures of all of which are incorporated in their entirety by reference herein.

TECHNICAL FIELD

The present invention relates to a fingerprint capture system, a fingerprint capture device, an image processing apparatus, a fingerprint capture method, and a storage medium.

BACKGROUND ART

Fingerprints have uniqueness and permanence because fingerprints are different among individuals and do not change in their lifetime. Thus, fingerprints have been widely used in the situations where identification of an individual is required. An optical device that captures a fingerprint by using a two-dimensional image sensor such as a Complementary Metal Oxide Semiconductor (CMOS) image sensor or the like is known as one of the devices for acquiring such a fingerprint.

Among the optical devices that capture a fingerprint by using an image sensor, a transmission type fingerprint input device has been focused on (see Patent Literature 1). In a transmission type fingerprint input device, a light from a light source is caused to enter a finger and is scattered therein, and a light exiting from the surface of the finger is utilized to capture an image of a fingerprint.

CITATION LIST

Patent Literature

PTL 1: Japanese Patent No. 3751872

SUMMARY OF INVENTION

Technical Problem

When a fingerprint is captured, however, the quality of a captured fingerprint image may vary due to a condition or the like at the capturing, and thus a low quality fingerprint image may be obtained. Since a low quality fingerprint image makes identification of an individual difficult, it is desirable for a fingerprint image to be of a higher quality as much as possible. An example of a low quality fingerprint image may be an image with an insufficient contrast between a ridge line part and a valley line part of a fingerprint or an image with uneven brightness. Further, an example of a low quality fingerprint image may be an image in which a part of a fingerprint may be deleted as a result of misalignment of a finger with respect to a region that can be captured by an image sensor at the capturing.

The present invention has been made in view of the above problem and intends to provide a fingerprint capture system, a fingerprint capture device, an image processing apparatus, a fingerprint capture method, and a storage medium that can acquire a high quality fingerprint image.

Solution to Problem

According to an example aspect of the present invention, provided is a fingerprint capture system including: a capture unit that captures a fingerprint; an image processing unit to which a fingerprint image of the fingerprint captured by the capture unit is transferred and that processes the fingerprint image; a display unit on which the fingerprint image transferred to the image processing unit is displayed; a recording unit in which the fingerprint image transferred to the image processing unit is recorded by the image processing unit; and an instruction unit that inputs, in the image processing unit, a record instruction that instructs the image processing unit to record the fingerprint image in the recording unit, and the image processing unit records, in the recording unit, the fingerprint image displayed on the display unit at the time when the record instruction is input by the instruction unit.

According to another example aspect of the present invention, provided is a fingerprint capture device including: a sensor unit that captures a fingerprint; a transfer unit that, in order to display a fingerprint image of the fingerprint captured by the sensor unit on a display unit, transfers the fingerprint image to an image processing unit; and an instruction unit that inputs, into the image processing unit, a record instruction that instructs recording of the fingerprint image transferred to the image processing unit and displayed on the display unit into a recording unit.

According to yet another example aspect of the present invention, provided is an image processing apparatus including: a receiving unit that receives a fingerprint image of a fingerprint captured by a capture unit that captures the fingerprint; a display control unit that displays the fingerprint image received by the receiving unit on a display unit; and a recording control unit that, based on a record instruction that instructs recording of the fingerprint image displayed on the display unit in a recording unit, records the fingerprint image in the recording unit.

According to yet another example aspect of the present invention, provided is a fingerprint capture method including: capturing a fingerprint; transferring a fingerprint image of the captured fingerprint; displaying the transferred fingerprint image; recording the transferred fingerprint image; and inputting a record instruction that instructs recording of the fingerprint image, and the recording of the fingerprint image records the fingerprint image displayed at the time when the record instruction is input.

According to yet another example aspect of the present invention, provided is a storage medium in which a program is stored, the program causing a computer that processes a fingerprint image transferred from a fingerprint capture device that captures a fingerprint to execute: displaying a fingerprint image transferred from the fingerprint capture device; and recording the fingerprint image transferred from the fingerprint capture device, and the recording records the fingerprint image displayed at the time when a record instruction that instructs recording of the fingerprint image is input.

Advantageous Effects of Invention

According to the present invention, a high quality fingerprint image can be acquired.

DESCRIPTION OF EMBODIMENTS

First Example Embodiment

A fingerprint capture system and a fingerprint capture method according to a first example embodiment of the present invention will be described by using FIG. 1 to FIG. 8.

Figure 1:
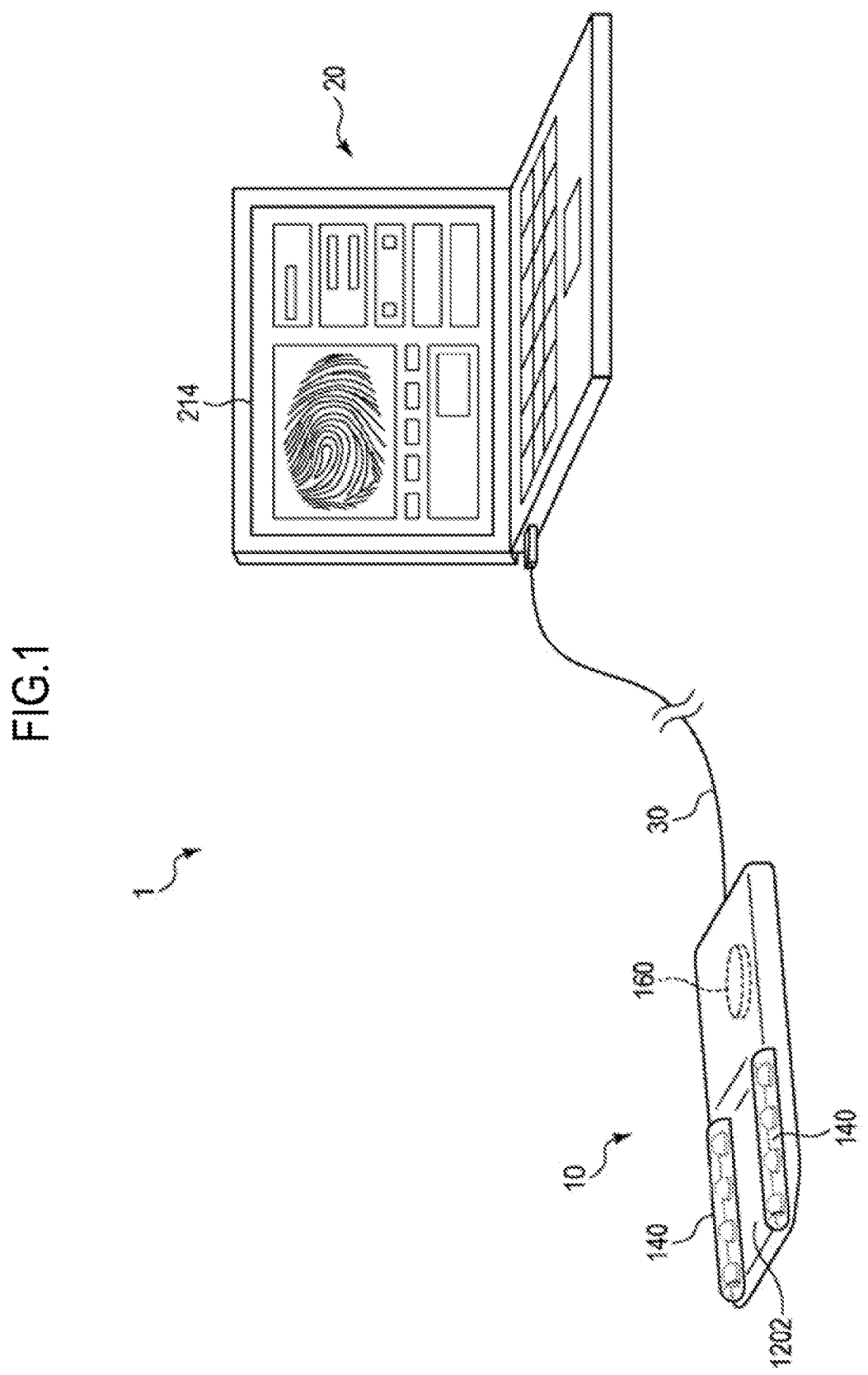
FIG. 1 is a schematic diagram illustrating a fingerprint capture system according to a first example embodiment of the present invention.

First, the general configuration of the fingerprint capture system according to the present example embodiment will be described by using FIG. 1. FIG. 1 is a schematic diagram illustrating the general configuration of the fingerprint capture system according to the present example embodiment.

As illustrated in FIG. 1, a fingerprint capture system 1 according to the present example embodiment has a fingerprint capture device 10 that captures a fingerprint of a subject and an image processing apparatus 20 that performs processes such as display, recording, or the like on a fingerprint image that is an image of a fingerprint captured by the fingerprint capture device 10. The image processing apparatus 20 has a display 214 that displays a fingerprint image. The fingerprint capture device 10 is communicably connected to the image processing apparatus 20 via the communication cable 30. Note that the fingerprint capture device 10 may be communicably connected to the image processing apparatus 20 by using a wireless scheme instead of a wired scheme through the communication cable 30.

A subject whose fingerprint is captured by the fingerprint capture system 1 according to the present example embodiment is not limited in particular, and any age of persons including a newborn, an infant, a young child, or the like whose finger is too thin, too small, too soft, or the like, which makes it difficult to capture their fingerprints, can be a subject. Note that it is impossible or difficult for a newborn, an infant, a young child, or the like to capture the fingerprint by himself/herself alone. When it is necessary to capture a fingerprint of such a subject who is incapable of or has difficulty in capturing the fingerprint by himself/herself alone, an adult or the like who is capable of operating the device would be an assisting person to assist the subject in capturing the fingerprint of the subject, as described later.

The fingerprint capture device 10 is an optical fingerprint scanner that functions as a capture unit that captures a fingerprint image by using a two-dimensional image sensor. The fingerprint capture device 10 can capture a fingerprint image of any one of respective thumbs, index fingers, middle fingers, ring fingers, and little fingers of the left hand and the right hand of a subject, namely, the ten fingers in total, for example. Further, the fingerprint capture device 10 can capture a fingerprint image of not only a finger of the hands but also any one of respective first toes, second toes, third toes, fourth toes, and fifth toes of the left foot and the right foot, namely, the ten fingers of feet (toes) in total.

When a newborn, an infant, or a young child is a subject, for example, the fingerprint capture device 10 can be used to capture fingerprints of a plurality of fingers or toes of a single subject and provide these fingerprint images of the plurality of fingers or toes for identification of an individual. In this case, for example, for a single subject, fingerprints of the thumb of the left hand, the thumb of the right hand, the first toe of the left foot, and the first toe of the right foot can be sequentially captured.

Figure 2:
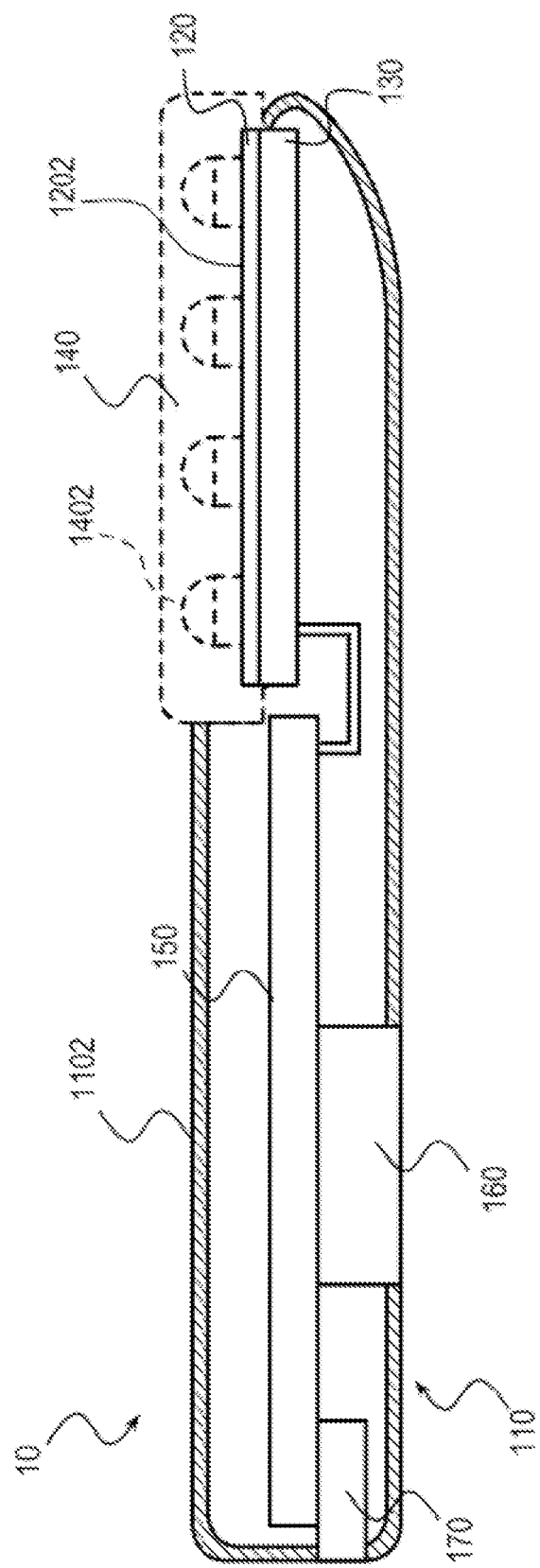
FIG. 2 is a sectional view illustrating a fingerprint capture device in the fingerprint capture system according to the first example embodiment of the present invention.
Figure 3:
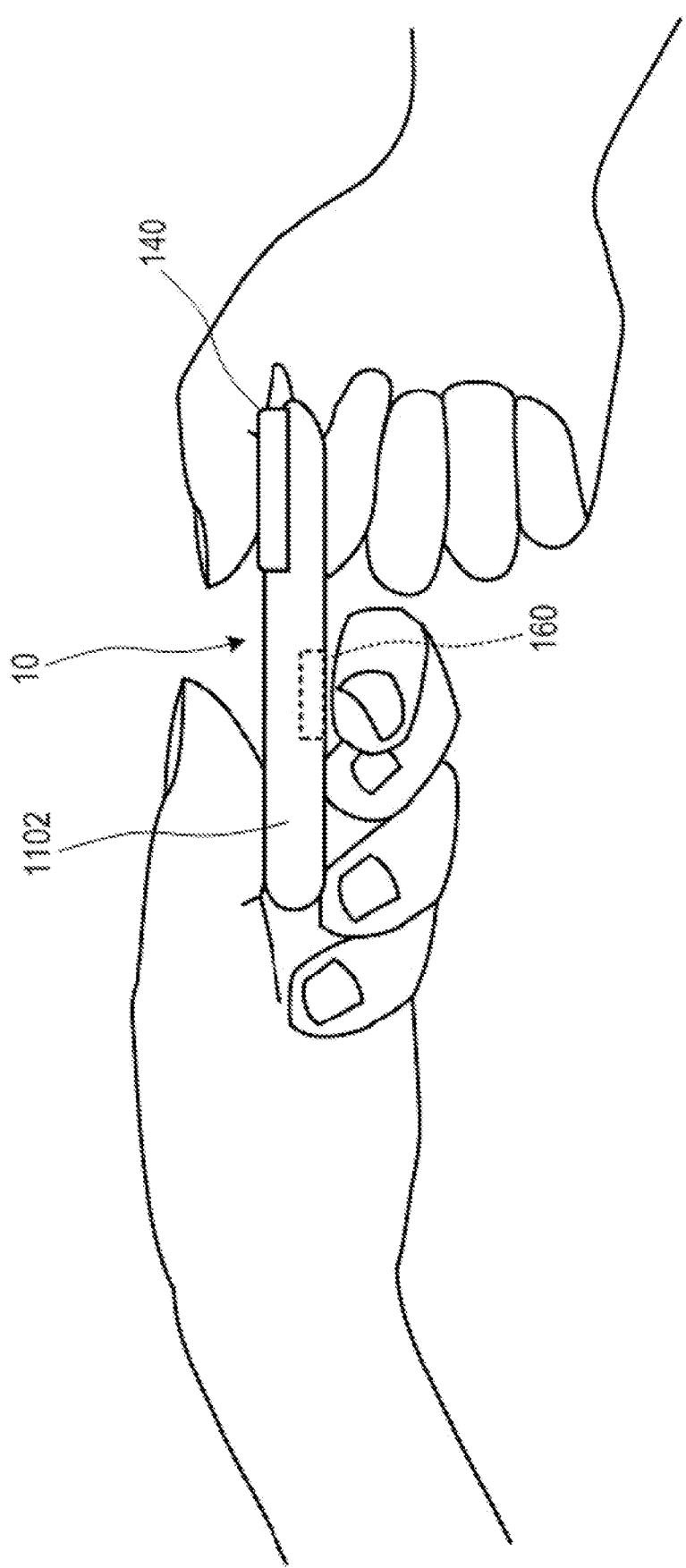
FIG. 3 is a schematic diagram illustrating a view in which an assisting person holds the fingerprint capture device in the fingerprint capture system according to the first example embodiment of the present invention to capture a fingerprint of a finger of a subject.
Figure 4:
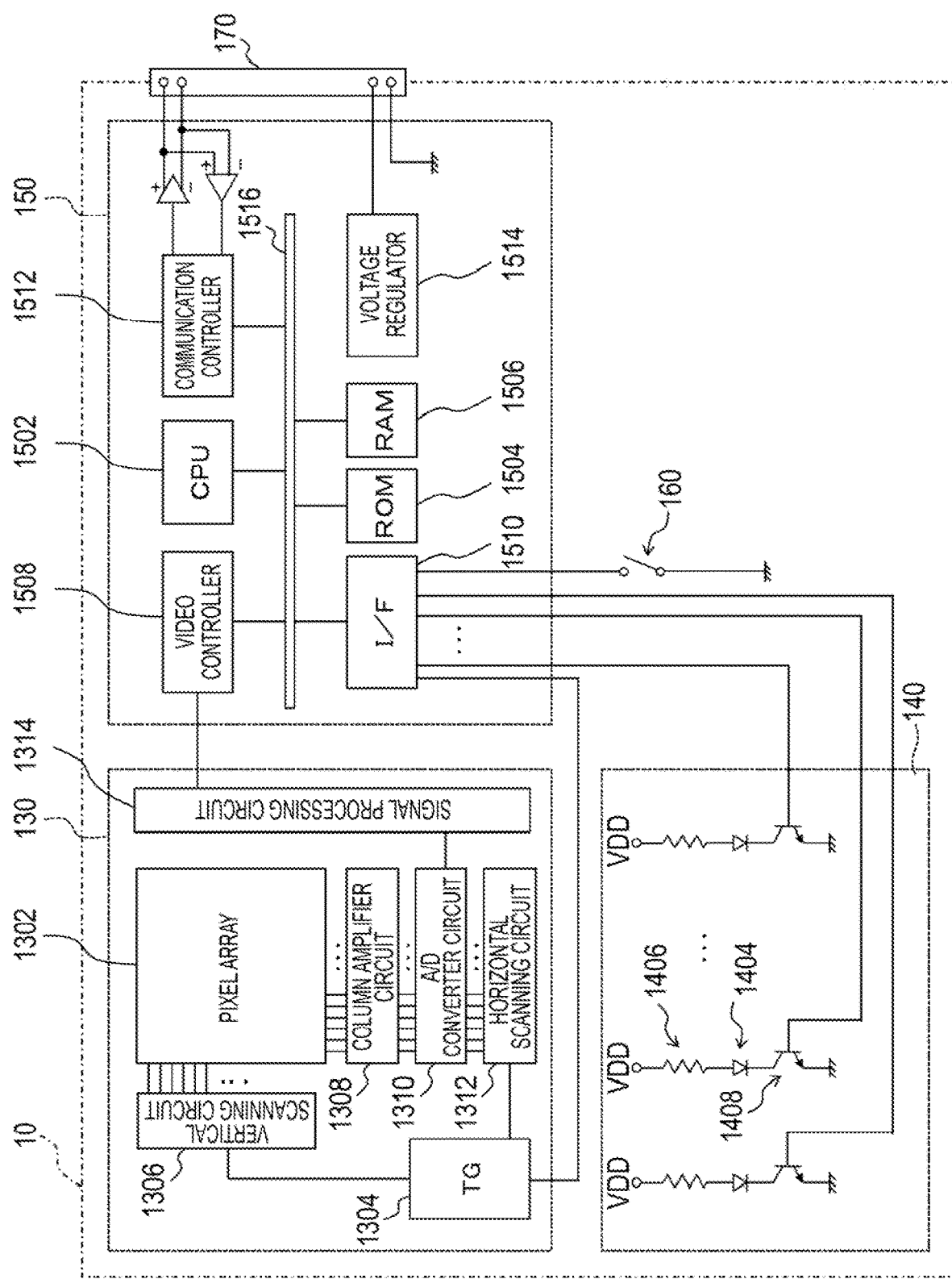
FIG. 4 is a block diagram illustrating the fingerprint capture device in the fingerprint capture system according to the first example embodiment of the present invention.

The specific configuration of the fingerprint capture device 10 will be described below by using FIG. 2 to FIG. 4. FIG. 2 is a sectional view illustrating the fingerprint capture device 10 and illustrates a cross section in a plane along the longitudinal direction and the vertical direction of the fingerprint capture device 10. FIG. 3 is a schematic diagram illustrating a view in which an assisting person holds the fingerprint capture device 10 to capture a fingerprint of a finger of a subject. FIG. 4 is a block diagram illustrating the fingerprint capture device 10.

As illustrated in FIG. 2, the fingerprint capture device 10 has a thin casing 110 shaped in a flat, approximate rectangular parallelepiped. A sensor cover 120 having an outer surface serving as a sensor face 1202 is provided on a top plate of the casing 110. The fingerprint capture device 10 has an imaging sensor 130 provided inside the casing 110 via the sensor cover 120, a pair of near-infrared light sources 140 provided on the top plate of the casing 110, and a control circuit 150 provided inside the casing 110.

A casing 110 is a hollow member having an external shape of a vertically flat, approximate rectangular parallelepiped, and the longitudinal direction is a front-back direction. Note that the front part of the casing 110 is tapered. The casing 110 is a resin member, for example. The external shape of the casing 110 is thin and narrow so that a person capable of operating the device can hold it by one hand. Note that the external shape of the casing 110 is not limited to the external shape of a flat, approximate rectangular parallelepiped, but any shape may be employed.

A rectangular sensor cover 120 is provided to the front part of the top plate of the casing 110. In the sensor cover 120, the outer surface serves as the sensor face 1202 with which the ball of the finger whose fingerprint is to be captured comes into contact. The rectangular sensor cover 120 is provided to the front part of the top plate of the casing 110 such that a pair of sides of the sensor cover 120 extend in the longitudinal direction. The sensor cover 120 is formed of a plate-like member whose material transmits a near-infrared light, for example, formed of a protection glass. Thereby, as described later, a near-infrared light is emitted from the near-infrared light source 140, enters a finger on the sensor cover 120, and is emitted from the ball of the finger after scattered inside the finger, and the scattered lights then enter the image sensor 130. The sensor cover 120 is contacted with the ball of a finger of a subject who directs his/her fingertip to the sensor cover 120 from the front side of the casing 110 when capturing a fingerprint.

The near-infrared light sources 140 are provided on the top plate of the casing 110 on both sides of the sensor cover 120, respectively. Each of the near-infrared light sources 140 has a plurality of light emitting diodes (LEDs) 1402.

The plurality of LEDs 1402 each emit a near-infrared light. The wavelength of the near-infrared light emitted by the LED 1402 is 820 to 980 nm, for example. The plurality of LEDs 1402 are provided so as to be aligned in lines in a longitudinal direction of the casing 110 with a predetermined spacing. Further, the plurality of LEDs 1402 are covered with a protective member having transparency to a near-infrared light. When capturing a fingerprint, each LED 1402 is turned on, near-infrared lights are emitted so as to expand upward from each LED 1402, and the finger whose ball is in contact with the sensor cover 120 is irradiated with the near-infrared lights.

Note that each LED 1402 may be provided inclined so as to emit a near-infrared light in an obliquely upward direction of the sensor cover 120 side. Further, the near-infrared light source 140 is not limited to the light source having a plurality of LEDs 1402, and a linear light source extending in the longitudinal direction of the casing 110 may be used as the near-infrared light source 140.

The image sensor 130 as a sensor unit that captures a fingerprint is provided inside the casing 110. The image sensor 130 is provided inside the casing 110 so as to direct the capturing surface to the sensor cover 120 provided on the top plate of the casing 110. The capturing surface of the image sensor 130 has a rectangular shape having a wider area than the ball of the finger (toe) whose fingerprint is to be captured. The image sensor 130 is configured to capture a fingerprint of a finger by light-receiving, at a capturing surface, near-infrared lights that have been irradiated from the ball of a finger contacting with the sensor cover 120 and have passed through the sensor cover 120. The image sensor 130 is a two-dimensional image sensor, for example, a CMOS image sensor. Further, other than the CMOS image sensor, a Charge Coupled Device (CCD) image sensor may be used as the image sensor. While the pixel density and the number of pixels of the image sensor 130 are not limited in particular, it is preferable that the density be high such as 1000 ppi or higher, for example, and that the number of pixels be large when considering a case of capturing a fingerprint of a newborn, an infant, a young child, and the like. Specifically, a large CMOS image sensor with a high pixel density and a large number of pixels that has a size of 2 cm in width, 3 cm in length and a pixel density of 1270 ppi, for example, can be used as the image sensor 130.

In the fingerprint capture device 10, the principle of a fingerprint being captured by the image sensor 130 is as follows. In capturing a fingerprint, near-infrared lights are emitted from the near-infrared light sources 140 with the ball of a finger being in contact with the sensor face 1202 of the sensor cover 120. The near-infrared lights emitted from the near-infrared light sources 140 enter the finger on the sensor cover 120. The near-infrared lights entering the finger are scattered inside the finger and then emitted out of the finger from the surface of the finger. The near-infrared lights emitted out of the finger have different intensities in accordance with whether emitted from the ridge line part or emitted from the valley line part of the fingerprint.

Since the ridge line part of a fingerprint is in contact with the sensor face 1202 of the sensor cover 120, the near-infrared light emitted out of the finger from the ridge line part reaches and enters the image sensor 130 at a relatively high intensity without significant attenuation. In contrast, since the valley line part of a fingerprint is not in contact with the sensor face 1202, the near-infrared light emitted out of the finger from the valley line part is scattered by an air layer present between the valley line part and the sensor face 1202. In addition, reflection and refraction occur due to the difference in the refractive index at the interfaces between the skin and the air and between the air and the sensor cover. Thus, the near infrared light emitted out of the valley line part is significantly attenuated compared to the near infrared light emitted out of the ridge line part and reaches and enters the image sensor 130 at a relatively low intensity or does not even reach the image sensor 130.

As a result, a fingerprint image in which there is a difference in brightness/darkness between the ridge line part and the valley line part of the fingerprint is captured on the image sensor 130. That is, in a captured fingerprint image, the ridge line parts of the fingerprint appear as bright parts, and the valley line parts appear as dark parts. Accordingly, a fingerprint is captured by receiving near-infrared lights scattered inside a finger emitted out of the finger by using the image sensor 130.

The image sensor 130 that has captured a fingerprint of a finger outputs image data forming a fingerprint image thereof. As described later, image data output from the image sensor 130 is transferred to the image processing apparatus 20 via the control circuit 150 and then via the communication cable 30. The image processing apparatus 20 to which image data is transferred performs display, recording, or the like of the fingerprint image based on the transferred image data.

The rear portion of the casing 110 serves as a holding portion 1102 held by a subject whose fingerprint is to be captured or an assisting person who assists capturing of the finger of the subject in capturing a fingerprint. In accordance with whether or not the subject whose fingerprint is to be captured is able to capture the fingerprint by himself/herself alone, the attitude of the subject in capturing the fingerprint will be different as described below.

First, when a subject is a person who is able to capture the fingerprint by himself/herself alone such as an adult, for example, the subject can cause the ball of the finger whose fingerprint is to be captured to come into contact with the sensor face of the sensor cover 120 while holding the holding portion 1102 by a hand opposite to the finger whose fingerprint is to be captured. The subject can hold the holding portion 1102 from the side such that, among the fingers of the hand holding the holding portion 1102, the thumb is positioned on the top plate side of the casing 110 and the four fingers other than the thumb are positioned on the bottom plate side of the casing 110, for example.

In contrast, for example, when a subject is a person who is unable to capture or has difficulty in capturing the fingerprint by himself/herself alone such as a newborn, an infant, a young child, or the like, an assisting person can assist capturing of a fingerprint of the finger of the subject. The assisting person is an adult or a minor who is able to operate the device by himself/herself alone. In this case, the assisting person holds the holding portion 1102 by one hand and moves the fingerprint capture device 10 toward the thumb of the subject whose fingerprint is to be captured. The assisting person can hold the holding portion 1102 from the side such that, among the fingers of the hand holding the holding portion 1102, the thumb is positioned on the top plate side and the four fingers other than the thumb are positioned on the bottom plate side of the casing 110, for example. Furthermore, as illustrated in FIG. 3, the assisting person can cause the ball of the finger of the subject to come into contact with the sensor face 1202 while using the other hand if necessary. Note that, although not illustrated in FIG. 3, the assisting person can use the fingertip or the like of his/her hand which holds the holding portion 1102 to press the finger of the subject that is in contact with the sensor face 1202 and fix the position thereof.

A press button type capture switch 160 that functions as an instruction unit is provided in the middle of the bottom face of the holding portion 1102 held by the subject or the assisting person. The capture switch 160 is configured so that, when pressed down, it can instruct the near-infrared light source 140 to be turned on or off, instruct the image sensor 130 to capture a fingerprint, or instruct the image processing apparatus 20 to record a fingerprint image. Signals input to the fingerprint capture device 10 and image processing apparatus 20 in response to pressing down of the capture switch 160 will be described later. The subject or the assisting person holding the holding portion 1102 can press down the capture switch 160 by any of the four fingers positioned on the bottom face side of the casing 110 of the fingers of the hand holding the holding portion 1102 while still holding the holding portion 1102.

Further, the capture switch 160 is formed so as to be embedded in the holding portion 1102 such that the pressed down face of the capture switch 160 and the bottom face of the holding portion 1102 are substantially flat. The capture switch 160 is provided so as not to project with respect to the bottom face of the holding portion 1102 as illustrated, which can suppress erroneous pressing down of the capture switch 160.

The control circuit 150 is accommodated inside the holding portion 1102 of the casing 110. Further, a connector portion 170 to which the communication cable 30 is connected is provided in the side end portion on the rear side of the holding portion 1102.

FIG. 4 is a block diagram illustrating each unit of the fingerprint capture device 10 described above and illustrates the details of the image sensor 130, the near-infrared light source 140, and the control circuit 150.

As illustrated in FIG. 4, the image sensor 130 has a pixel array 1302 and a timing generator 1304. Further, the image sensor 130 has a vertical scanning circuit 1306, a column amplifier circuit 1308, an analog-to-digital (A/D) converter circuit 1310, a horizontal scanning circuit 1312, and a signal processing circuit 1314.

A plurality of pixels are provided in a matrix in the pixel array 1302. Each pixel has a photoelectric conversion element that generates a pixel signal by photoelectrically converting an incident near-infrared light. The timing generator 1304 generates and outputs a timing signal used for controlling the vertical scanning circuit 1306 and the horizontal scanning circuit 1312. The vertical scanning circuit 1306 scans the pixels of the pixel array 1302 on a pixel row basis. The column amplifier circuit 1308 amplifies pixel signals read out by scans performed by the vertical scanning circuit 1306. The A/D converter circuit 1310 converts pixel signals amplified by the column amplifier circuit 1308 from analog signals to digital signals. The horizontal scanning circuit 1312 performs scans on a pixel column basis to read out pixel signals converted by the A/D converter circuit 1310 to the outside. The signal processing circuit 1314 performs predetermined signal processing on the pixel signal read out by the horizontal scanning circuit 1312 and output from the A/D converter circuit 1310 to output image data forming a fingerprint image. The image data output from the signal processing circuit 1314 is input to the control circuit 150.

In the near-infrared light source 140, a current limiting resistor 1406 that restricts a current flowing in the LED 1402 and a transistor 1408 that serves as a switch are connected to each of the plurality of LEDs 1402.

One of the terminals of the current limiting resistor 1406 is connected to the anode side terminal of each LED 1402. The collector of each transistor 1408 is connected to the cathode side terminal of each LED 1402. A positive power source voltage VDD is input to the other terminal of each current limiting resistor 1406. The base of each transistor 1408 is connected to the control circuit 150, and the transistor 1408 is switched to be turned on and off by a switch signal input to the base from the control circuit 150.

The control circuit 150 has a central processing unit (CPU) 1502, a read only memory (ROM) 1504, and a random access memory (RAM) 1506. Further, the control circuit 150 has a video controller 1508, an interface (I/F) 1510, and a communication controller 1512. Furthermore, the control circuit 150 has a voltage regulator 1514. The CPU 1502, the ROM 1504, the RAM 1506, the video controller 1508, the I/F 1510, and the communication controller 1512 are connected to a common bus line 1516.

The CPU 1502 executes a program for controlling the operation of the fingerprint capture device 10 to control the operation of each unit of the fingerprint capture device 10. The ROM 1504 stores a program executed by the CPU 1502. Further, the RAM 1506 is a working area when the CPU 1502 executes a program.

The video controller 1508 is connected to the signal processing circuit 1314 of the image sensor 130, and image data is input from the signal processing circuit 1314. The video controller 1508 transfers image data to the communication controller 1512 via the bus line 1516.

The timing generator 1304 of the image sensor 130 is connected to the I/F 1510. Thereby, the control signal by the CPU 1502 is input to the timing generator 1304 via the I/F 1510. The timing generator 1304 generates and outputs a timing signal based on a control signal input via the I/F 1510.

Further, the bases of the plurality of transistors 1408 in the near-infrared light source 140 are connected to the I/F 1510. Thereby, the switch signal from the CPU 1502 is input to the base of the transistors 1408 via the I/F 1510. The transistor 1408 is switched to be turned on and off based on a switch signal input via the I/F 1510. In response to the transistor 1408 being switched to be turned on and off, the LED 1402 is switched to be turned on and off, and thereby the near-infrared light source 140 is switched to be turned on and off.

Further, the capture switch 160 is connected to the I/F 1510. In response to the capture switch 160 being pressed down, output of a control signal and a switch signal by the CPU 1502 is triggered. Further, in response to the capture switch 160 being pressed down, a fingerprint image is recorded in the image processing apparatus 20 as described later.

Specifically, in a non-operating state of the image sensor 130, the near-infrared light source 140 is also in a turn-off state, and pressing down of the capture switch 160 under this state causes the near-infrared light source 140 to be turned off and start capturing a fingerprint by the image sensor 130. The image sensor 130 that has started capturing a fingerprint captures the fingerprint at a constant time interval and outputs image data of the fingerprint image.

Further, once the capture switch 160 is pressed down during the image sensor 130 being capturing a fingerprint at a constant time interval, the fingerprint image displayed on the display 214 in the image processing apparatus 20 is recorded as described later. Then, when the fingerprint image has been recorded and the image sensor 130 enters a non-operating state, capturing of the fingerprint by the image sensor 130 ends.

The communication controller 1512 functions as a transfer unit configured to transfer image data of the fingerprint image, which transfers image data transferred from the video controller 1508 to the image processing apparatus 20 via the communication cable 30 connected to the connector unit 170. The communication controller 1512 is configured to communicate with the image processing apparatus 20 via the communication cable 30 in accordance with a communication standard such as Universal Serial Bus (USB) or the like, for example.

The communication cable 30 is configured to have two differential signal lines for transmitting and receiving signals, a power source line for power supply, and a ground line. The communication controller 1512 transmits and receives signals through the two differential signal lines in the communication cable 30.

The power source line of the communication cable 30 is connected to the voltage regulator 1514, and power is supplied via the power source line from a power source circuit 216 (see FIG. 5) in the image processing apparatus 20. The voltage regulator 1514 adjusts the voltage of the supplied power and supplies it as a power source to each unit of the fingerprint capture device 10. The fingerprint capture device 10 is of a bus-power system so as to operate by power supplied via the communication cable 30 from the image processing apparatus 20. Note that the fingerprint capture device 10 may be operated by power supplied from a built-in battery, for example, without limited to the bus-power system.

On the other hand, the image processing apparatus 20 functions as an image processing unit that performs processes such as display, recording, or the like on a fingerprint image transferred from the fingerprint capture device 10 that has captured a fingerprint. The image processing apparatus 20 may be formed of a personal computer (PC) of a laptop type, a tablet type, or the like, for example. Further, image processing apparatus 20 can control the operation of the fingerprint capture device 10. Note that the image processing apparatus 20 is not necessarily to be required to include the display 214 described later, and the image processing unit can be configured as including no display unit.

Figure 5:
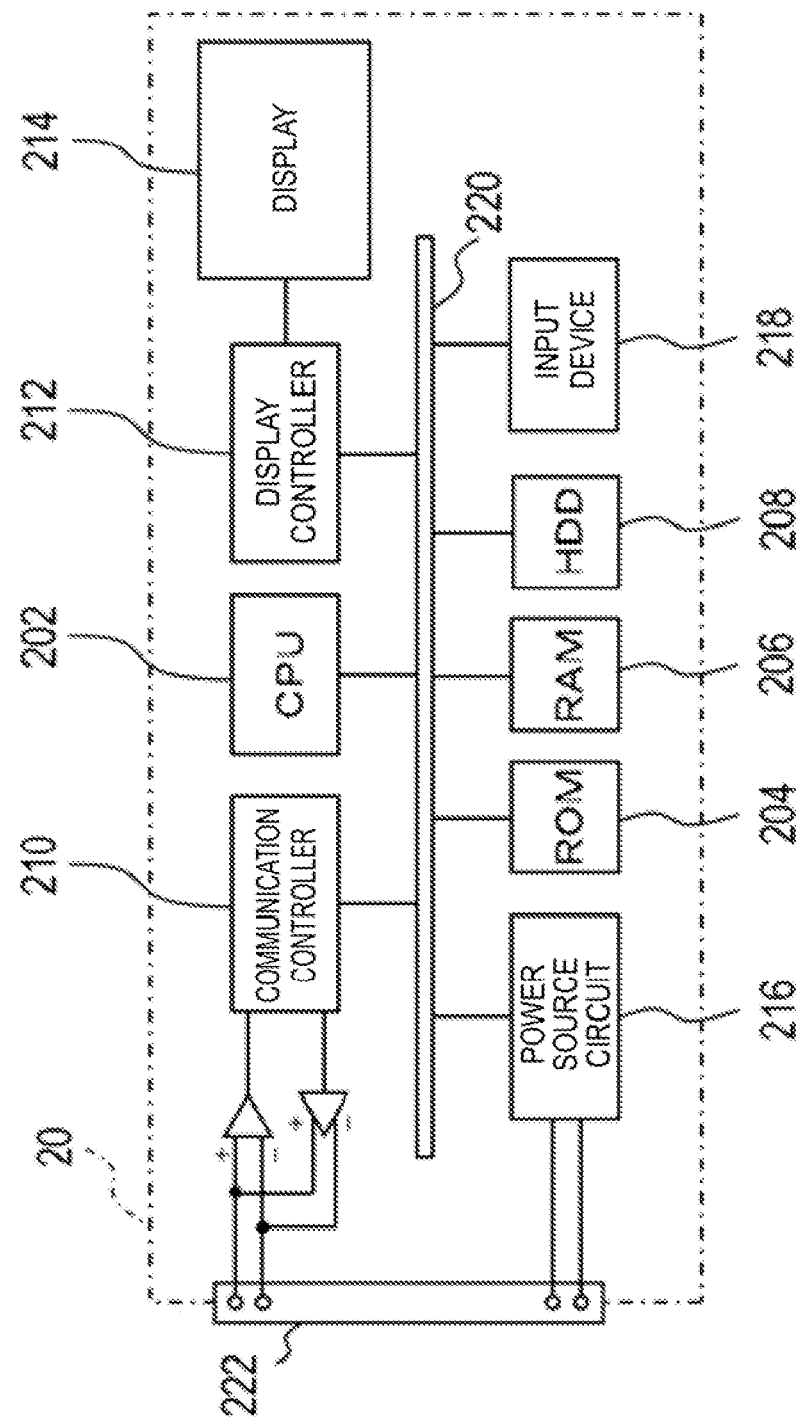
FIG. 5 is a block diagram illustrating an image processing apparatus in the fingerprint capture system according to the first example embodiment of the present invention.
Figure 6:
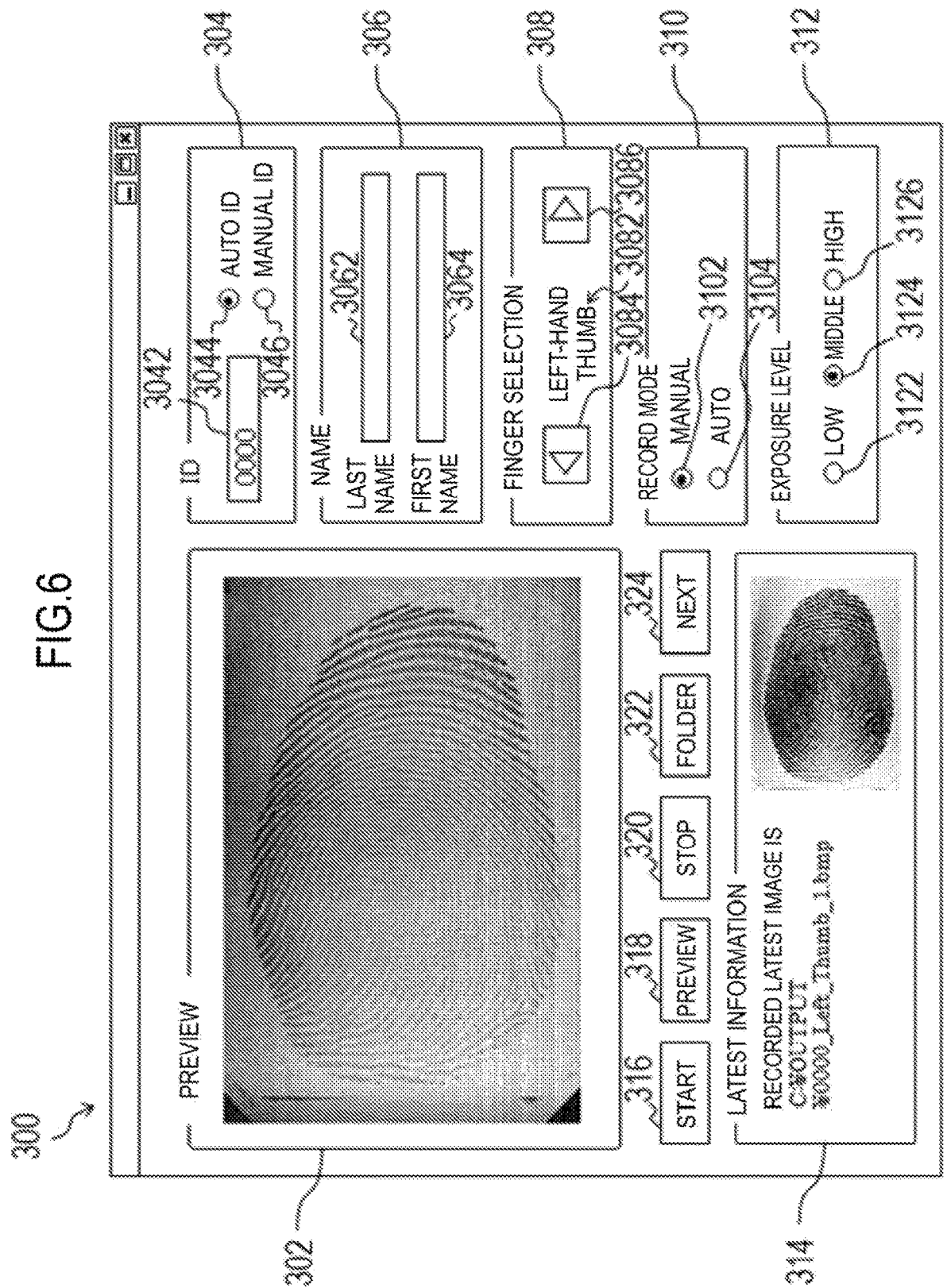
FIG. 6 is a schematic diagram illustrating a display window displayed on the image processing apparatus in the fingerprint capture system according to the first example embodiment of the present invention.

The specific configuration of the image processing apparatus 20 will be further described below by using FIG. 5 and FIG. 6. FIG. 5 is a block diagram illustrating the imaging processing apparatus 20. FIG. 6 is a schematic diagram illustrating a display window displayed on the image processing apparatus 20.

As illustrated in FIG. 5, the image processing apparatus 20 has a CPU 202, a ROM 204, a RAM 206, a hard disk drive (HDD) 208, and a communication controller 210. Further, the image processing apparatus 20 has a display controller 212 and the display 214. Further, the image processing apparatus 20 has the power source circuit 216 and an input device 218. The CPU 202, the ROM 204, the RAM 206, the HDD 208, the communication controller 210, display controller 212, the power source circuit 216, and the input device 218 are connected to a common bus line 220. Further, a connector unit 222 to which the communication cable 30 is connected is provided to the image processing apparatus 20.

The CPU 202 controls the entire operation of the image processing apparatus 20. Further, the CPU 202 executes an image processing program used for display, recording, or the like of a fingerprint image acquired by the fingerprint capture device 10. The image processing program performs image processing on image data transferred from the fingerprint capture device 10 and performs display, recording, or the like on a fingerprint image thereof.

The ROM 204 stores therein a program such as a boot program. The RAM 206 is used as a working area when the CPU 202 executes a program. Further, the RAM 206 functions as an image memory in which image data of a fingerprint image transferred from the fingerprint capture device 10 is temporarily stored. The HDD 208 stores a program such as an image processing program executed by the CPU 202.

Further, the HDD 208 functions as a recording unit that records a fingerprint image captured by the fingerprint capture device 10. The CPU 202 functions as a record control unit to record a fingerprint image in the HDD 208. Note that the recording unit that records a fingerprint image is not limited to the HDD 208 and, instead of the HDD 208, various recording devices may be used as the recording unit. The recording unit that records a fingerprint image may be built in the image processing apparatus 20 similarly to the HDD 208 or may be an independent external recording device separate from the image processing apparatus 20.

The communication controller 210 functions as a receiving unit that receives image data of a fingerprint image to receive image data transferred from the communication controller 1512 of the fingerprint capture device 10 via the communication cable 30 connected to the connector unit 222. The image data received by the communication controller 210 is temporarily stored in the RAM 206 as an image memory. The communication controller 210 is configured to communicate with the fingerprint capture device 10 via the communication cable 30 in accordance with a communication standard such as USB or the like, for example, in association with the communication controller 1512. The communication controller 210 is configured to transmit and receive signals by two differential signal lines in the communication cable 30 in association with the communication controller 1512.

Further, the display 214 that functions as a display unit that displays a fingerprint image is connected to the display controller 212. The display controller 212 cooperates with the CPU 202 to function as a display control unit and renders and displays a display window of an image processing program executed by the CPU 202 on the display 214. The display window of the image processing program displayed on the display 214 includes a preview window in which a captured fingerprint image is displayed. Note that, while not limited in particular, the display 214 is a liquid crystal display, for example. Further, the display 214 may be built in the image processing apparatus 20, which is a laptop PC, a tablet PC, or the like, or may be an external display provided separately from the image processing apparatus 20.

The power source circuit 216 supplies power of a built-in power source of the image processing apparatus 20 or power of an external power source connected to the image processing apparatus 20 to the fingerprint capture device 10. The power source circuit 216 is connected to the power source line and the ground line of the communication cable 30 and supplies power to the voltage regulator 1514 of the fingerprint capture device 10 via the power source line.

The input device 218 is a keyboard, a mouse, or the like, for example. Further, the input device 218 may be a touch panel embedded in the display 214. An operator can input text information such as an identification number (ID), a name, or the like of a subject or select information regarding the type of a finger in the image processing program displayed on the display 214 via the input device 218. Further, setting of capturing conditions or the like may be performed.

FIG. 6 illustrates an example of a display window 300 of an image processing program displayed on the display 214 of the image processing apparatus 20. As illustrated in FIG. 6, the display window 300 is provided with a preview window 302, an identification number (ID) entry area 304, a name entry area 306, a finger type selection area 308, a recording mode selection area 310, and an exposure level setting area 312. Further, a latest-information display area 314 is provided in the display window 300. Further, the display window 300 is provided with a start button 316, a preview button 318, a stop button 320, a folder selection button 322, and a next button 324.

The preview window 302 displays a preview of a fingerprint image captured by the fingerprint capture device 10. In the preview window 302, a fingerprint image can be displayed such that the light-dark of ridge line parts captured as bright parts and valley line parts captured as dark parts is inverted in terms of visibility. Note that a fingerprint image can be displayed without a change of the light-dark of the ridge line parts and the valley line parts captured by the fingerprint capture device 10.

The ID entry area 304 is an area to which an ID of a subject whose fingerprint is to be captured is input. The ID entry area 304 is provided with an ID entry field 3042 to which an ID is input and two radio buttons 3044 and 3046 used for selecting an entry scheme of the ID. When the radio button 3044 labeled with "Auto ID" is selected, an ID can be automatically input in the ID entry field 3042. Further, when the radio button 3046 labeled with "Manual ID" is selected, an ID can be manually input in the ID entry field 3042 through the input device 218. For example, the input ID is utilized as a part of a file name of a fingerprint image recorded in the HDD 208 or is recorded in a database managed by the image processing program. Note that the database is recorded in the HDD 208.

The name entry area 306 is an area to which the name of a subject whose fingerprint is to be captured is input. The name input area 306 is provided with a family name input field 3062 to which a family name of a subject is input and a first name entry field 3064 to which a first name of a subject is input. The input name is recorded in a database managed by an image processing program, for example.

The finger type selection area 308 is an area used for selecting the type of a finger whose fingerprint is to be captured. The finger type selection area 308 is provided with a finger type display field 3082 in which a finger type is displayed and switching buttons 3084 and 3086 used for switching a finger type displayed in the finger type display field 3082. The finger type to be displayed in the finger type display field 3082 can be switched by pressing switching buttons 3084 and 3086. A finger type to be displayed can be switched and selected out of the thumbs, the index fingers, the middle fingers, the ring fingers, and the small fingers of the left hand and the right hand, respectively, and the first toes, the second toes, the third toes, the fourth toes, and the fifth toes of the left foot and the right foot, respectively, namely, 20 fingers in total. The finger type displayed in the finger type display field 3082 and selected is utilized as a part of a file name of a fingerprint image recorded in the HDD 208 or is recorded in a database managed by the image processing program, for example.

The recording mode selection area 310 is an area used for selecting and setting a mode by which a captured fingerprint image is recorded. The recording mode selection area 310 is provided with two radio buttons 3102 and 3104 used for selecting a recording mode. A recording mode which records a fingerprint image in the HDD 208 can be set manually by selecting the radio button 3102 labeled with "Manual", that is, in accordance with a record instruction input by the capture switch 160 of the fingerprint capture device 10 as described later. Further, a recording mode which automatically records a fingerprint image in the HDD 208 can be set by selecting the radio button 3104 labeled with "Auto". Note that, in the present example embodiment, a fingerprint image is recorded manually as described later.

The exposure level setting area 312 is an area used for setting an exposure level when capturing a fingerprint by the fingerprint capture device 10. The exposure level setting area 312 is provided with, for example, three radio buttons 3122, 3124, and 3126 used for setting an exposure level. For example, three radio buttons 3122, 3124, and 3126 are labeled with "low", "middle", and "high", respectively, and an exposure level can be set in three steps. Selection of the radio button 3122 labeled with "low" allows the lowest exposure level to be set. Also, selection of the radio button 3126 labeled with "high" allows the highest exposure level to be set. Also, selection of the radio button 3124 labeled with "middle" allows the intermediate exposure level of three steps to be set. Note that an exposure level can be realized by changing the capturing time period by the image sensor 130 or changing the output of the near-infrared light source 140 in accordance with the setting of the exposure level, for example.

In the latest-information display area 314, a file name of the latest fingerprint image recorded in the HDD 208 is displayed including a path of a recording folder, for example. Further, in the latest-information display area 314, the latest fingerprint image recorded in the HDD 208 is displayed, for example. Note that a folder of the HDD 208 in which a fingerprint image is recorded can be selected from a folder selection window displayed by pressing the folder selection button 322. Furthermore, the quality of a fingerprint image displayed in the preview window 302 or a recorded fingerprint image may be displayed in the latest-information display area 314.

Further, in the display window 300, the state of the fingerprint capture device 10 can be checked by pressing the start button 316, and capturing by the fingerprint capture device 10 can be stopped by pressing the stop button 320. Furthermore, the fingerprint capture device 10 can be started up by pressing the preview button 318. Further, the ID in the ID entry field 3042 can be changed or cleared to move onto capturing a fingerprint of the next subject by pressing the next button 324.

The fingerprint capture system 1 according to the present example embodiment is configured as above. In the fingerprint capture system 1 according to the present example embodiment, when the capture switch 160 provided in the fingerprint capture device 10 is pressed down, start of capturing, stop of capturing, or recording of a fingerprint image by the fingerprint capture device 10 is controlled.

Figure 7:
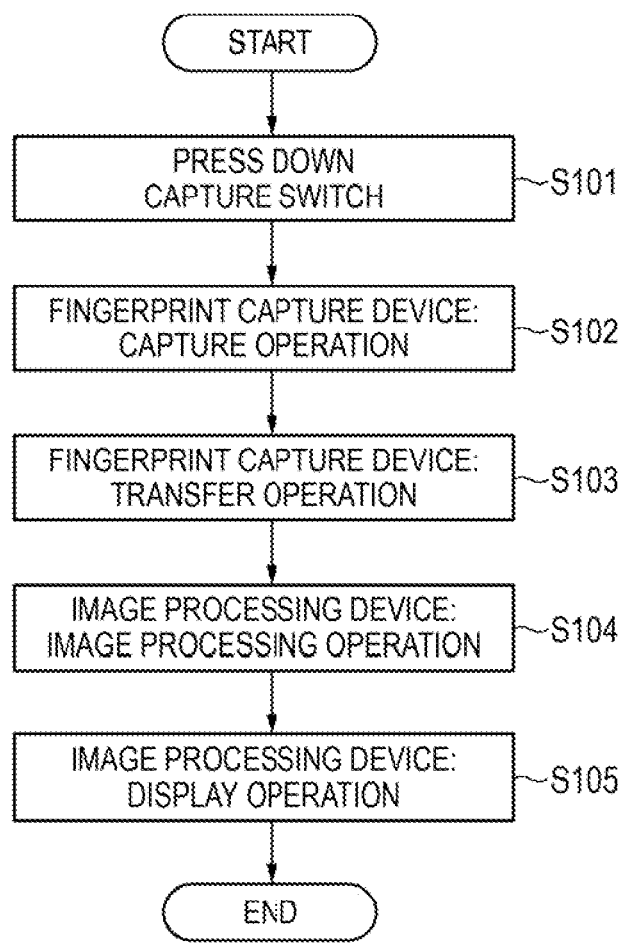
FIG. 7 is a flowchart illustrating a basic operation of the fingerprint capture system according to the first example embodiment of the present invention.
Figure 8:
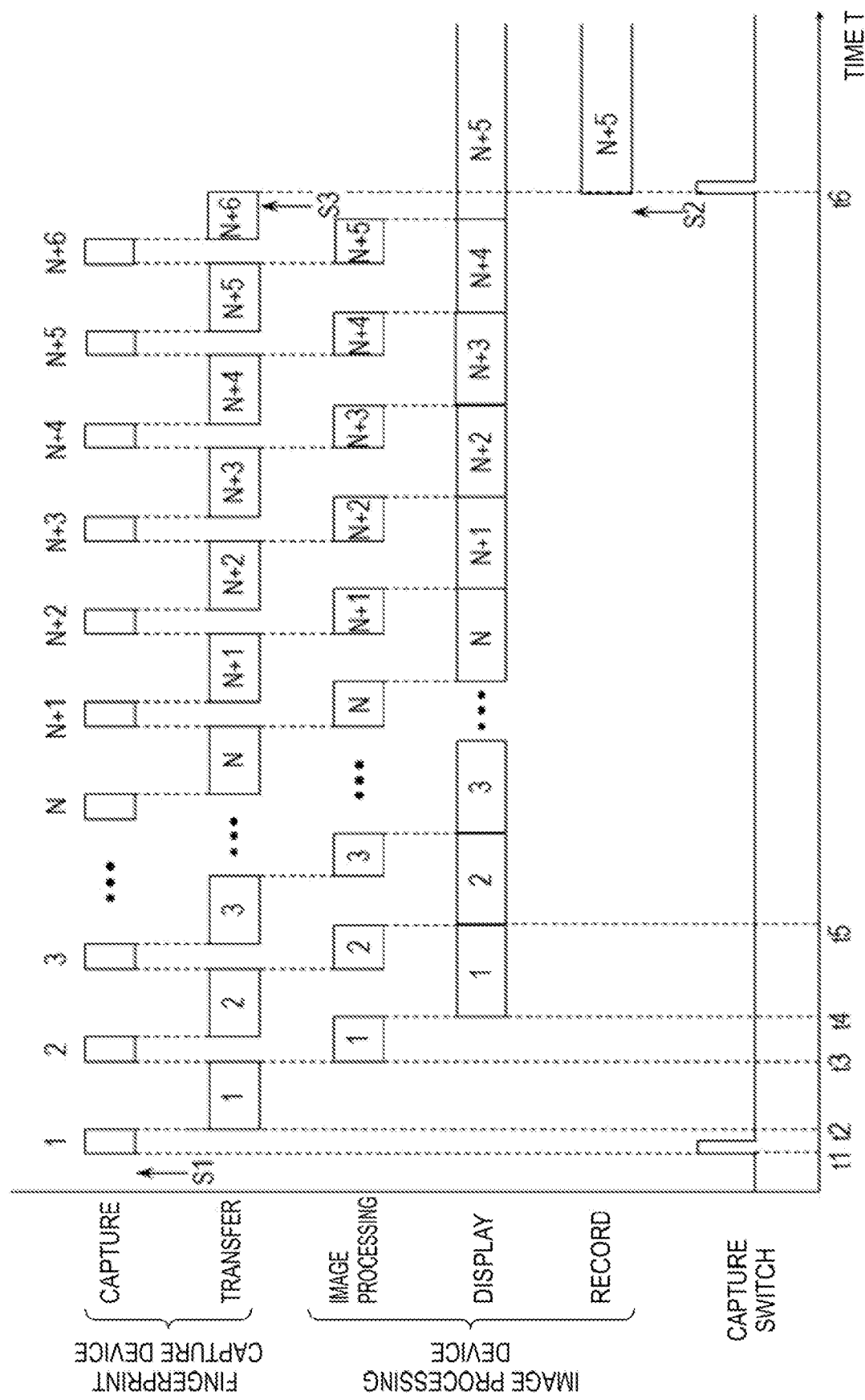
FIG. 8 is a timing chart illustrating the operation of the fingerprint capture device and the image processing apparatus of the fingerprint capture system according to the first example embodiment of the present invention.

Next, a fingerprint capture method using the fingerprint capture system 1 according to the present example embodiment described above will be further described by using FIG. 7 and FIG. 8. FIG. 7 is a flowchart illustrating a basic operation of the fingerprint capture system 1 according to the present example embodiment. FIG. 8 is a timing chart illustrating the operation of the fingerprint capture device 10 and the image processing apparatus 20 in the fingerprint capture system 1 according to the present example embodiment.

First, prior to the description of the fingerprint capture method according to the present example embodiment, the basic operation of the fingerprint capture system 1 will be described by using FIG. 7. The basic operation here corresponds to an operation until a fingerprint image captured by the image capture device 10 is displayed on the display 214 of the image processing apparatus 20. Further, in the following description, a subject who performs capturing of his/her fingerprint by himself/herself and an assisting person who helps capturing of the fingerprint of the subject are referred to as an operator.

First, in a state where the fingerprint capture device 10 is stopped, the operator has the ball of his/her finger whose fingerprint is to be captured come into contact with the sensor face 1202 of the fingerprint capture device 10.

Next, in a state where the ball of the finger is in contact with the sensor face 1202 of the fingerprint capture device 10, the operator presses down the capture switch 160 provided to the fingerprint capture device 10 as illustrated in FIG. 7 (step S101). This first pressing down of the capture switch 160 causes a signal illustrating a capture instruction that instructs capturing to be input to the fingerprint capture device 10.

In response to the signal indicating the capture instruction input by the first pressing down of the capture switch 160, the fingerprint capture device 10 drives the image sensor 130 and turns on the near-infrared light source 140. Thereby, the fingerprint capture device 10 performs a capture operation of capturing a fingerprint image (step S102). In the capture operation, the fingerprint capture device 10 captures, repeatedly at a constant time interval, a fingerprint of the same finger whose ball is in contact with the sensor face 1202. While varying depending on the performance of the image sensor 130 used, the capturing time period required for the fingerprint capture device 10 to capture one fingerprint image is 0.6 to 1 second, for example.

Further, upon capturing a fingerprint image, the fingerprint capture device 10 performs a transfer operation of transferring image data of the captured fingerprint image to the image processing apparatus 20 (step S103). In the transfer operation, the fingerprint capture device 10 transfers image data of the captured fingerprint image to the image processing apparatus 20 via the communication cable 30.

The image processing apparatus 20 to which image data of the fingerprint image is transferred temporarily stores the image data in the RAM 206 as an image memory and then performs an image processing operation of performing predetermined image processing on the image data (step S104).

Next, the image processing apparatus 20 performs a display operation of displaying a fingerprint image on the display 214 (step S105). In the display operation, the image processing apparatus 20 displays a fingerprint image for a predetermined display time on the display 214. In the display 214, a fingerprint image is displayed in the preview window 302 in the display window 300 of the image processing program. The display time in which a fingerprint image is displayed is the time period enough for the operator to review the displayed fingerprint image to determine whether or not the quality of the fingerprint image is good.

The display time period in which one fingerprint image is displayed on the display 214 is longer than or equal to the capturing time period required for the fingerprint capture device 10 to capture one fingerprint image. For example, when the capturing time period per fingerprint image is 0.6 seconds, for example, the display time period per fingerprint image on the display 214 can also be around 0.6 seconds, which is close the capturing time period. With such a length of display time period, the operator can review the quality of a fingerprint image displayed on the display 214 to determine whether or not the quality thereof is good.

Further, with a further longer display time period of a fingerprint image than the capturing time period, the operator can thoroughly determine whether or not the quality of the fingerprint image is good. Thus, the display time period per fingerprint image can be set longer than the capturing time period per fingerprint image. The time for having the display time period longer than the capturing time period may be generated on the fingerprint capture device 10 side or may be generated on the image processing apparatus 20 side. For example, a delay circuit that delays transfer of image data is provided in the fingerprint capture device 10 to delay the time required to transfer image data from the fingerprint capture device 10 to the image processing apparatus 20, and thereby the display time can be increased in accordance with the delay time. Further, also in the image processing apparatus 20, it is possible to generate the delay time in a hardware manner by using a delay circuit or the like or in a software manner by using an image processing program or the like and increase the display time period in accordance with the delay time. However, since the longer the display time period is, the lower the efficiency of acquiring a fingerprint is, it is preferable to set the display time period taking a viewpoint of the efficiency of acquiring a fingerprint into consideration.

Once the capture switch 160 is pressed down, the fingerprint capture system 1 according to the present example embodiment repeats the basic operation described above from capturing to display of a fingerprint image for the same finger whose ball is in contact with the sensor face 1202. Thereby, a plurality of fingerprint images of the same finger sequentially captured by the fingerprint capture device 10 are sequentially displayed for a predetermined display time period on the display 214 of the image processing apparatus 20. In the display 214, after a fingerprint image is displayed for a predetermined display time period, which is switched to the next display of another fingerprint image. The fingerprint capture system 1 according the present example embodiment repeats the above-described basic operation until the capture switch 160 is pressed down for the second time. When the capture switch 160 is pressed down for the second time, the image processing apparatus 20 performs a record operation of recording the fingerprint image.

A fingerprint capture method according to the present example embodiment including the record operation of the image processing apparatus 20 will be described below by using FIG. 8. In the timing chart illustrated in FIG. 8, the horizontal axis represents time t. Further, in the timing chart illustrated in FIG. 8, among the first stage to the sixth stage arranged downward, solid-line frames in the first stage represent the capture operation performed by the fingerprint capture device 10. Solid-line frames in the second stage represent the transfer operation performed by the fingerprint capture device 10. Solid-line frames in the third stage represent the image processing operation performed by the image processing apparatus 20. Solid-line frames in the fourth stage represent the display operation performed by the image processing apparatus 20. Solid-line frames in the fifth stage represent the record operation performed by the image processing apparatus 20. Further, the numbers N (where N is a natural integer) provided to the solid-line frames on each stage of the first stage to the fifth stage indicate that the operation represented by the solid-line frame is an operation for the N-th frame fingerprint image captured for the N-th time. Further, in the sixth stage, it is indicated that the capture switch 160 of the fingerprint capture device 10 is pressed down at the time when a signal transitions from a low level to a high level and thereby a pulse occurs.

As illustrated in FIG. 8, at the time t1, in response to the operator pressing down the capture switch 160 for the first time, a signal S1 indicating a startup instruction that instructs a startup is input to the fingerprint capture device 10. Once the signal S1 indicating a startup instruction is input, the control circuit 150 supplies a power source voltage to the image sensor 130 and starts up the image sensor 130. The control circuit 150 turns on the transistor 1408 to turn on the LED 1402. Each pixel of the pixel array 1302 receives lights scattered inside the finger and accumulates charges in accordance with the light amount. The vertical scanning circuit 1306 scans the pixel array 1302 on a row basis, and the column amplifier circuit 1308 amplifies pixel signals output from respective row. The A/D convertor circuit 1310 converts pixel signals amplified by the column amplifier circuit 1308 from an analog signal to a digital signal and outputs the pixel signals to the signal processing circuit 314 sequentially in accordance with a control signal from the horizontal scanning circuit 1312. The signal processing circuit 1314 performs image processing such as correlated double sampling, shading correction, or the like on the pixel signal and accumulates the pixel signals of the first frame as a fingerprint image.

At the time t2, upon the completion of capturing of the fingerprint image of the first frame, the control circuit 150 starts transmitting the fingerprint image of the first frame to the image processing apparatus 20 on a packet basis. That is, the video controller 1508 sequentially reads out the fingerprint image accumulated in the signal processing circuit 1314 and sends it out to the communication controller 1512.

The communication controller 1512 divides the fingerprint image into packets and transmits the packets to the image processing apparatus 20 via the communication cable 30. In the image processing apparatus 20, the communication controller 210 receives the fingerprint image on a packet basis, and the CPU 202 sequentially accumulates the received packets in the RAM 206.

At the time t3, after the fingerprint capture device 10 has transmitted the whole fingerprint image of the first frame to the image processing apparatus 20, the fingerprint capture device 10 starts capturing a fingerprint image of the second frame. The image processing apparatus 20 performs image processing on the fingerprint images accumulated in the RAM 206. The image processing may include, for example, a determination process as to whether or not a fingerprint image is properly captured, in addition to noise removal, normalization of brightness values, and binarization. Note that, while the image processing apparatus 20 is performing image processing, the fingerprint capture device 10 captures the fingerprint image of the second frame.

At the time t4, upon the completion of image processing on the fingerprint image of the first frame, the image processing apparatus 20 displays, on the display 214, the fingerprint image of the first frame resulted after the image processing. Meanwhile, the fingerprint capture device 10 transmits the fingerprint image of the second frame to the image processing apparatus 20 on a packet basis, and the image processing apparatus 20 performs image processing on the received fingerprint image.

At the time t5, upon the completion of image processing on the fingerprint image of the second frame, the image processing apparatus 20 displays the fingerprint image of the second frame on the display 214.

The image processing apparatus 20 repeats the image processing operation and the display operation every time image data of the fingerprint image is transferred from the fingerprint capture device 10 as described above. Meanwhile, the operator can review the fingerprint image displayed on the display 214 of the image processing apparatus 20. Thereby, for the displayed fingerprint image, the operator can determine whether or not the quality is good, respectively.

The operator reviews the quality of a plurality of fingerprint images sequentially displayed on the display 214 and presses down the capture switch 160 when a fingerprint image determined to be of high quality is displayed on the display 214. In FIG. 8, the fingerprint image of the first frame to the fingerprint image of the (N+5)-th frame are sequentially displayed on the display 214 with elapsing of time. Then, at the time t6 when the fingerprint image of the (N+5)-th frame is displayed, the operator determines that the fingerprint image of the (N+5)-th frame is of high quality and presses down the capture switch 160 for the second time.

When the operator presses down the capture switch 160 for the second time, a signal S2 indicating a record instruction that instructs recording of a fingerprint image is input to the image processing apparatus 20. When the signal S2 indicating a record instruction is input, the image processing apparatus 20 records the fingerprint image displayed on the display 214 in the HDD 208. Further, the image processing apparatus 20 maintains a state where the fingerprint image recorded in the HDD 208 is displayed on the display 214. In FIG. 8, the fingerprint image of the (N+5)-th frame displayed on the display 214 at the time t6 is recorded, and the state where the fingerprint image of the (N+5)-th frame is displayed on the display 214 is maintained.

When the operator presses down the capture switch 160 for the second time, the signal S2 indicating a record instruction is input, and a signal S3 indicating a stop instruction that instructs stop is input to the fingerprint capture device 10. When the signal S3 indicating a stop instruction is input, the fingerprint capture device 10 enters a stop state to stop the capture operation or the transfer operation. In FIG. 8, the transfer operation is stopped for the captured fingerprint image of the (N+6)-th frame.

Accordingly, the fingerprint image displayed on the display 214 is recorded in the HDD 208, and acquisition of a fingerprint image is stopped.

As discussed above, in the present example embodiment, the fingerprint image displayed on the display 214 at the time when the capture switch 160 is pressed down for the second time is recorded in the HDD 208. At the same time, the fingerprint capture device 10 stops power source supply to the image sensor 130 to cause the image sensor 130 to enter a stop state. The captured fingerprint image is kept on being displayed on the display 214. According to the present example embodiment, since it is possible to review the quality of a fingerprint image on the display 214 and then record the fingerprint image, a high quality fingerprint image can be acquired.

In general, there is a predetermined delay time from the time when a fingerprint is captured by the fingerprint capture device 10 to the time when image data of the captured fingerprint image is transferred to the image processing apparatus 20 and the fingerprint image is displayed on the display 214. This delay time is due to the time period required to transfer image data, the time period required for image processing, or the like. In the present example embodiment, since it is necessary to capture fingerprint images of various sizes from a newborn to an infant at a sufficient resolution, it is necessary to increase the number of pixels of the image sensor 130. The image sensor 130 has a size of 2 cm in width and 3 cm in length and a pixel density of 1270 ppi, for example. This causes a longer transfer time for image data of a fingerprint image, and it may take 0.6 seconds per frame including the transfer time and other processing time to transfer image data of a fingerprint image with such a large number of pixels in the current USB 2.0 standard, for example. Thus, if a fingerprint image currently being captured or a fingerprint image subsequently captured by the fingerprint capture device 10 were recorded in the HDD 208 in response to the second pressing down of the capture switch 160, there would be an inconsistency between a fingerprint image to be recorded and a fingerprint image being displayed on the display 214. Therefore, in such a case, the operator is unable to review the quality of a fingerprint image to be recorded in the HDD 208 to determine whether or not the quality is good, and the low quality fingerprint image may be recorded.

In contrast, in the present example embodiment, since a fingerprint image displayed on the display 214 is recorded in the HDD 208 as described above, the operator is able to review the quality of the fingerprint image on the display 214 to determine whether or not the quality is good.

In particular, when the subject is a child such as a newborn, an infant, or a young child, a sufficient contrast may not be obtained in the fingerprint image because the finger thereof is thin, small, soft, or the like. Further, since children may move their finger during capturing due to unstable behavior, brightness unevenness may occur or a part of a fingerprint may be deleted in a fingerprint image. According to the present example embodiment, since it is possible to review the quality of a fingerprint image to be recorded and then record the fingerprint image, even when the subject is a child such as a newborn, an infant, or a young child, it is possible to review and determine the quality of a plurality of fingerprint images and record a high quality fingerprint image among the plurality of fingerprint images.

Further, even with the shortened delay time described above allowed by an improved data transfer rate due to advancement of technologies, it is desirable to ensure a sufficient display time period for the operator to determine on the display 214 whether or not the quality of a fingerprint image is good. In the present example embodiment, a fingerprint image transferred from the fingerprint capture device 10 to the image processing apparatus 20 and displayed on the display 214 is recorded in the HDD 208. Thus, according to the present example embodiment, a sufficient display time period to determine whether or not the quality is good can be ensured without restricted by the timing or the like of capturing by the fingerprint capture device 10.

Note that an image processing circuit may be provided to the fingerprint capture device 10, and it is possible to perform image processing such as binarization or the like on the fingerprint image by using the image processing circuit and then transfer image data of the fingerprint image from the fingerprint capture device 10 to the image processing apparatus 20. This can improve the transfer speed of image data of fingerprint images from the fingerprint capture device 10 to the image processing apparatus 20.

Further, when the subject is a child such as a newborn, an infant, or a young child, for example, repetition of capturing of fingerprint until a high quality fingerprint image is acquired may cause a large burden on the subject. According to the present example embodiment, since the quality is reviewed on the display 214 and then the fingerprint image is recorded in the HDD 208, retry of acquisition of fingerprint images can be avoided. Therefore, according to the present example embodiment, a high quality fingerprint image can be acquired at a high efficiency. Thus, according to the present example embodiment, when the subject is a child such as a newborn, an infant, or a young child in particular, a burden on the subject can be reduced.

Second Example Embodiment

A fingerprint capture system and a fingerprint capture method according to a second example embodiment of the present invention will be described by using FIG. 9. Note that similar elements to those in the fingerprint capture system and the fingerprint capture method according to the above-described first example embodiment are labeled with the same reference numerals, and the description thereof will be omitted or simplified.

The fingerprint capture system according to the present example embodiment is substantially similar to the fingerprint capture system according to the first example embodiment. The fingerprint capture system according to the present example embodiment is different from the fingerprint capture system according to the first example embodiment in that the image processing apparatus 20 reduces a plurality of fingerprint images with a constant time interval and then displayed on the display 214.

The fingerprint capture method using the fingerprint capture system according to the present example embodiment will be described below by using FIG. 9. FIG. 9 is a timing chart illustrating the operation of the fingerprint capture device 10 and the image processing apparatus 20 in the fingerprint capture system according to the present example embodiment. Note that the detail of the horizontal axis and the detail of the first stage to the sixth stage arranged downward of the timing chart illustrated in FIG. 9 are the same as those of the timing chart illustrated in FIG. 8.

Figure 9:
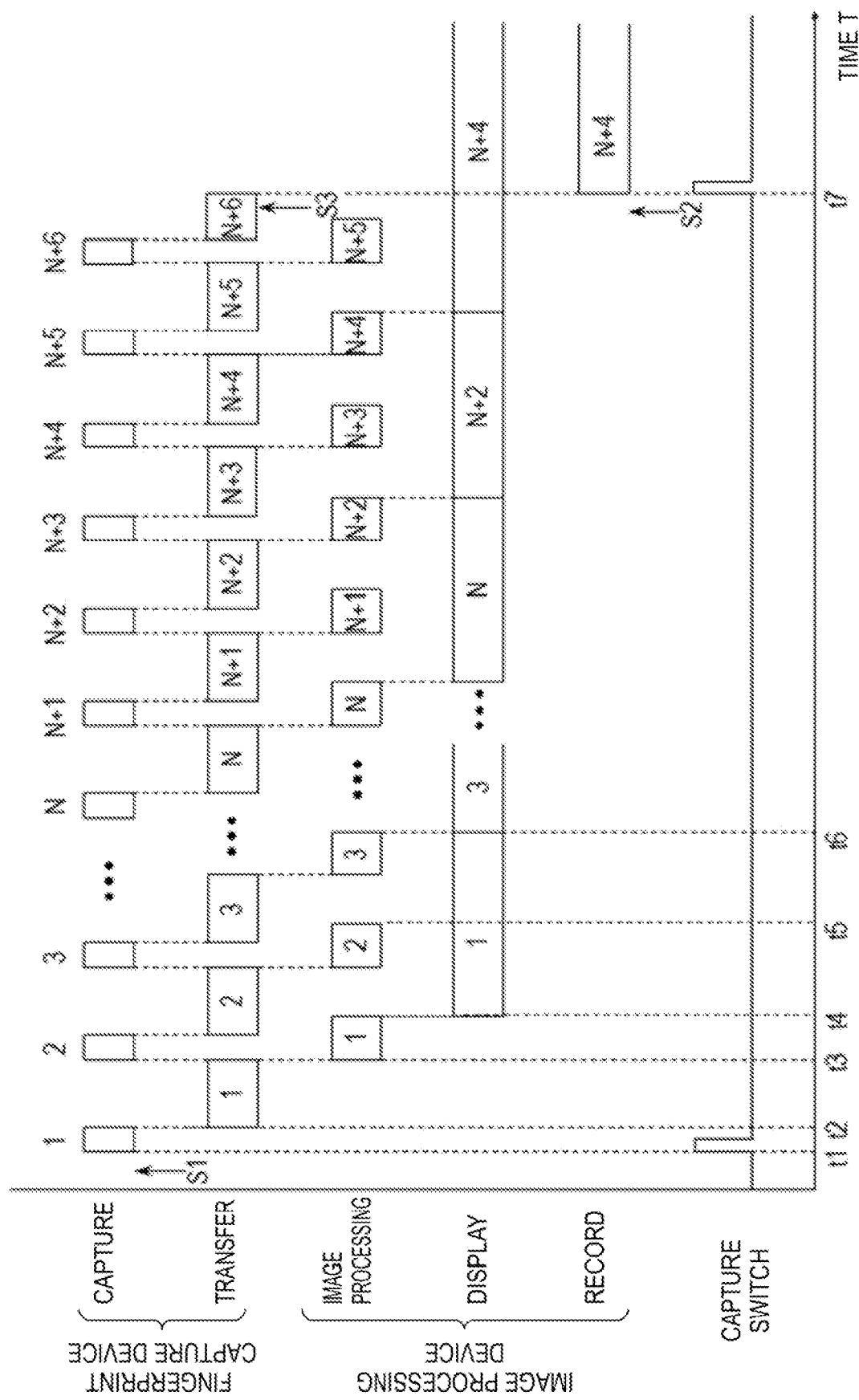
FIG. 9 is a timing chart illustrating the operation of a fingerprint capture device and an image processing apparatus of a fingerprint capture system according to a second example embodiment of the present invention.

As illustrated in FIG. 9, at the time t1, in response to the operator pressing down the capture switch 160 for the first time, in a similar manner to the first example embodiment, pixel signals of the first frame are accumulated as a fingerprint image in the signal processing circuit 1314.

At the time t2, upon the completion of capturing of the fingerprint image of the first frame, in a similar manner to the first example embodiment, the control circuit 150 starts transmitting the fingerprint image of the first frame to the image processing apparatus 20 on a packet basis. Further, in the image processing apparatus 20, the communication controller 210 receives the fingerprint image on a packet basis, and the CPU 202 sequentially accumulates the received packets in the RAM 206.

At the time t3, after the fingerprint capture device 10 has transmitted the whole fingerprint image of the first frame to the image processing apparatus 20, in a similar manner to the first example embodiment, the fingerprint capture device 10 starts capturing a fingerprint image of the second frame. The image processing apparatus 20 performs image processing on the fingerprint image accumulated in the RAM 206. Note that, while the image processing apparatus 20 is performing image processing, the fingerprint capture device 10 captures the fingerprint image of the second frame.

At the time t4, upon the completion of image processing on the fingerprint image of the first frame, the image processing apparatus 20 displays, on the display 214, the fingerprint image of the first frame resulted after the image processing. Meanwhile, the fingerprint capture device 10 transmits the fingerprint image of the second frame to the image processing apparatus 20 on a packet basis, and the image processing apparatus 20 performs image processing on the received fingerprint image.

Unlike the first example embodiment, however, at the time t5, even after the image processing apparatus 20 has completed the image processing on the fingerprint image of the second frame, the image processing apparatus 20 continues to display the fingerprint image of the first frame without displaying the fingerprint image of the second frame on the display 214. Display of the fingerprint image of the first frame continues until image processing of the third frame ends at the time t6.

At the time t6, upon the completion of image processing on the fingerprint image of the third frame, the image processing apparatus 20 displays the fingerprint image of the image-processed third frame on the display 214.

Accordingly, the image processing apparatus 20 repeats display of the sequentially captured multiple fingerprint images for every other frame.

As discussed above, in the present example embodiment, unlike the first example embodiment, the image processing apparatus 20 deletes image-processed multiple fingerprint images at a constant time interval and displays the reduced fingerprint images on the display 214. That is, the image processing apparatus 20 deletes the image-processed multiple fingerprint images every predetermined number of fingerprint images and displays the reduced fingerprint images on the display 214. In FIG. 9, the captured fingerprint images are reduced every other fingerprint image and displayed. Since the fingerprint images are reduced every other fingerprint image, the display time period per fingerprint image is longer than in the case of the first example embodiment. Note that the number of fingerprint images to be deleted at a constant time interval may be one fingerprint image or may be a plurality of fingerprint images captured continuously.

As discussed above, in the present example embodiment, not all of the plurality of fingerprint images sequentially captured by the fingerprint capture device 10 are displayed on the display 214, and the plurality of fingerprint images sequentially captured by the fingerprint capture device 10 are reduced at a constant time interval and displayed. Therefore, according to the present example embodiment, further sufficient display time period is ensured for the operator to review the quality of the fingerprint image on the display 214 to determine whether or not the quality is good. Therefore, according to the present example embodiment, acquisition of a high quality fingerprint image can be further ensured.

In a similar manner to the first example embodiment, the operator reviews the quality of a plurality of fingerprint images sequentially displayed on the display 214 and presses down the capture switch 160 when a fingerprint image determined to be of high quality is displayed on the display 214. In FIG. 9, the fingerprint image of the first frame, the fingerprint image of the third frame, . . . , a fingerprint image of the N-th frame, a fingerprint image of the (N+2)-th frame, and a fingerprint image of the (N+4)-th frame are sequentially displayed on the display 214 with elapsing of time. Then, at the time t7 when the fingerprint image of the (N+4)-th frame is displayed, the operator determines that the fingerprint image of the (N+4)-th frame is of high quality and presses down the capture switch 160 for the second time.

When the operator presses down the capture switch 160 for the second time, in a similar manner to the first example embodiment, a signal S2 indicating a record instruction that instructs recording of a fingerprint image is input to the image processing apparatus 20. When the signal S2 indicating a record instruction is input, the image processing apparatus 20 records the fingerprint image displayed on the display 214 in the HDD 208 in a similar manner to the first example embodiment. Further, the image processing apparatus 20 maintains a state where the fingerprint image recorded in the HDD 208 is displayed on the display 214. In FIG. 9, the fingerprint image of the (N+4)-th frame displayed on the display 214 at the time t7 is recorded, and the state where the fingerprint image of the (N+4)-th frame is displayed on the display 214 is maintained.

Further, when the operator presses down the capture switch 160 for the second time, the signal S2 indicating a record instruction is input, and a signal S3 indicating a stop instruction that instructs stop is input to the fingerprint capture device 10 in a similar manner to the first example embodiment. When the signal S3 indicating a stop instruction is input, the fingerprint capture device 10 enters a stop state to stop the capture operation or the transfer operation in a similar manner to the first example embodiment. In FIG. 9, the transfer operation is stopped for the captured fingerprint image of the (N+6)-th frame.

Accordingly, the fingerprint image displayed on the display 214 is recorded in the HDD 208, and acquisition of a fingerprint image is stopped.

Third Example Embodiment

A fingerprint capture system and a fingerprint capture method according to a third example embodiment of the present invention will be described by using FIG. 10. Note that similar elements to those in the fingerprint capture system and the fingerprint capture method according to the above-described first example embodiment are labeled with the same reference numerals, and the description thereof will be omitted or simplified.

The fingerprint capture system according to the present example embodiment is substantially similar to the fingerprint capture system according to the first example embodiment. The fingerprint capture system according to the present example embodiment is different from the fingerprint capture system according to the first example embodiment in that the image processing apparatus 20 determines whether or not the quality of fingerprint images is good and reduces the fingerprint images based on the quality of the fingerprint images for display on the display 214.

The fingerprint capture method using the fingerprint capture system according to the present example embodiment will be described below by using FIG. 10. FIG. 10 is a timing chart illustrating the operation of the fingerprint capture device 10 and the image processing apparatus 20 in the fingerprint capture system according to the present example embodiment. Note that the detail of the horizontal axis and the detail of the first stage to the sixth stage arranged downward of the timing chart illustrated in FIG. 10 are the same as those of the timing chart illustrated in FIG. 8.

Figure 10:
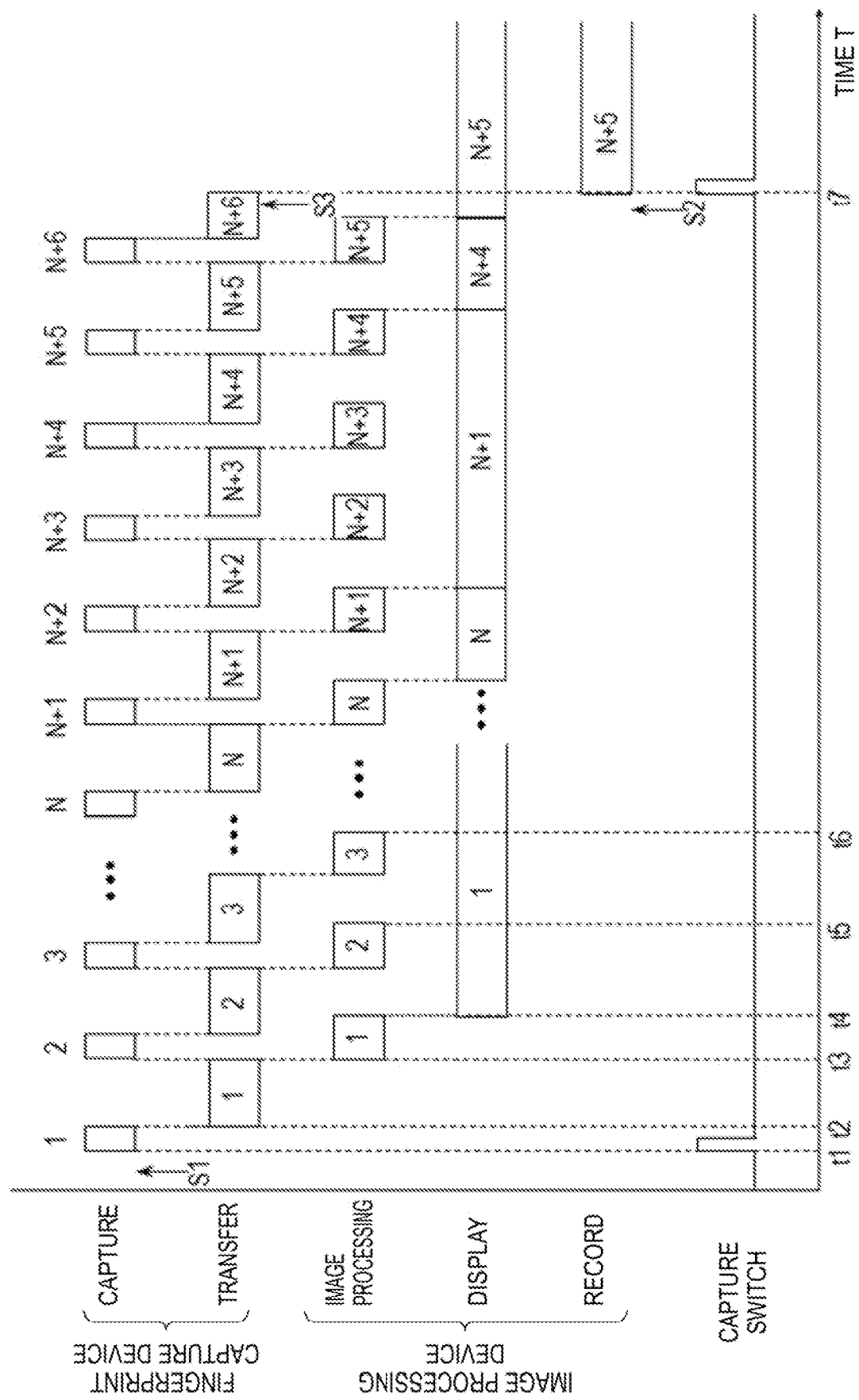
FIG. 10 is a timing chart illustrating the operation of a fingerprint capture device and an image processing apparatus of a fingerprint capture system according to a third example embodiment of the present invention.

As illustrated in FIG. 10, at the time t1, in response to the operator pressing down the capture switch 160 for the first time, in a similar manner to the first example embodiment, pixel signals of the first frame are accumulated as a fingerprint image in the signal processing circuit 1314.

At the time t2, upon the completion of capturing of the fingerprint image of the first frame, in a similar manner to the first example embodiment, the control circuit 150 starts transmitting the fingerprint image of the first frame to the image processing apparatus 20 on a packet basis. Further, in the image processing apparatus 20, the communication controller 210 receives the fingerprint image on a packet basis, and the CPU 202 sequentially accumulates the received packets in the RAM 206.

At the time t3, after the fingerprint capture device 10 has transmitted the whole fingerprint image of the first frame to the image processing apparatus 20, in a similar manner to the first example embodiment, the fingerprint capture device 10 starts capturing a fingerprint image of the second frame. The image processing apparatus 20 performs image processing on the fingerprint image accumulated in the RAM 206. Note that, while the image processing apparatus 20 is performing image processing, the fingerprint capture device 10 captures a fingerprint image of the second frame.

At the time t4, upon the completion of image processing on the fingerprint image of the first frame, the image processing apparatus 20 determines whether or not the quality of the fingerprint image of the first frame is good.

As discussed above, in the present example embodiment, unlike the first example embodiment, the image processing apparatus 20 performs an image processing operation and functions as a quality determination unit that determines whether or not the quality of a fingerprint image is good. The image processing apparatus 20 evaluates the contrast of a fingerprint image, brightness unevenness, or the like by using an image processing program and determines whether or not the quality of a fingerprint image is good. As a result of the quality determination, the image processing apparatus 20 determines that a fingerprint image having a quality which does not satisfy a predetermined quality is a low quality fingerprint image. Note that an image evaluation scheme used in the quality determination of a fingerprint image in the image processing apparatus 20 is not limited in particular, and various image processing schemes may be used. For example, in a fingerprint image represented by binary values, when the ratio of white regions and black regions is out of a predetermined range, it can be determined that no fingerprint is captured. Further, a typical fingerprint image may be pre-stored as model data, the similarity between the captured fingerprint image and the model data may be calculated, and a frame whose similarity is out of a standard may be removed.

As a result of the quality determination, for a plurality of fingerprint images, the image processing apparatus 20 does not display fingerprint images which is determined as a low quality fingerprint image and sequentially displays other fingerprint images having a quality above a predetermined quality on the display 214. In FIG. 10, the image processing apparatus 20 determines a fingerprint image of the first frame obtained after the quality determination as a fingerprint image having a quality above the predetermined quality and displays the fingerprint image of the first frame on the display 214. Meanwhile, the fingerprint capture device 10 transmits a fingerprint image of the second frame to the image processing apparatus 20 on a packet basis, and the image processing apparatus 20 performs image processing and quality determination on the received fingerprint image.

At the time t5, the image processing apparatus 20 completes the image processing and quality determination on the fingerprint image of the second frame. As a result, when determining the fingerprint image of the second frame as a low quality fingerprint image, the image processing apparatus 20 does not display the fingerprint image of the second frame on the display 214. In this case, the image processing apparatus 20 continues to display the fingerprint image of the first frame.

Furthermore, at the time t6, the image processing apparatus 20 completes processing and quality determination on a fingerprint image captured after the fingerprint image of the second frame. As a result, when determining the fingerprint image of a third frame as a low quality fingerprint image, the image processing apparatus 20 does not display the fingerprint image of the third frame on the display 214. In this case, the image processing apparatus 20 continues to display the fingerprint image of the first frame.

The display of the fingerprint image of the first frame is continued until a fingerprint image of a new frame is determined as a fingerprint image having a quality above a predetermined quality.

At the time t6, upon the completion of image processing on the fingerprint image of the third frame, the image processing apparatus 20 displays the image-processed fingerprint image of the third frame on the display 214.

As a result of the quality determination, out of a plurality of fingerprint images, the image processing apparatus 20 does not display fingerprint images determined to be low quality fingerprint images and sequentially displays the remaining fingerprint images above a predetermined quality on the display 214, as described above. In FIG. 10, out of the captured fingerprint images, the fingerprint image of the second frame, the fingerprint image of the third frame, the fingerprint image of a (N+2)-th frame, and the fingerprint image of a (N+3)-th frame are determined as low quality fingerprint images, respectively, and none of which is displayed.

As discussed above, according to the present example embodiment, since fingerprint images having a quality above a predetermined quality out of a plurality of fingerprint images are displayed on the display 214, the operator can select a higher quality fingerprint image from the displayed fingerprint images in a more reliable manner. Therefore, according to the present example embodiment, acquisition of a high quality fingerprint image can be further ensured.

In a similar manner to the first example embodiment, the operator reviews the quality of a plurality of fingerprint images sequentially displayed on the display 214 and presses down the capture switch 160 when a fingerprint image determined to be of high quality is displayed on the display 214. In FIG. 10, the fingerprint image of the first frame, . . . , the fingerprint image of the N-th frame, the fingerprint image of the (N+1)-th frame, a fingerprint image of the (N+4)-th frame, and a fingerprint image of the (N+5)-th frame are sequentially displayed on the display 214 with elapsing of time. Then, at the time t7 when the fingerprint image of the (N+5)-th frame is displayed, the operator determines that the fingerprint image of the (N+5)-th frame is of high quality and presses down the capture switch 160 for the second time.

When the operator presses down the capture switch 160 for the second time, in a similar manner to the first example embodiment, a signal S2 indicating a record instruction that instructs recording of fingerprint images is input to the image processing apparatus 20. When the signal S2 indicating a record instruction is input, the image processing apparatus 20 records the fingerprint image displayed on the display 214 in the HDD 208 in a similar manner to the first example embodiment. Further, the image processing apparatus 20 maintains a state where the fingerprint image recorded in the HDD 208 is displayed on the display 214. In FIG. 10, the fingerprint image of the (N+5)-th frame displayed on the display 214 at the time t7 is recorded, and the state where the fingerprint image of the (N+5)-th frame is displayed on the display 214 is maintained.

Further, when the operator presses down the capture switch 160 for the second time, and a signal S3 indicating a stop instruction that instructs stop is input to the fingerprint capture device 10 in a similar manner to the first example embodiment. When the signal S3 indicating a stop instruction is input, the fingerprint capture device 10 enters a stop state to stop the capture operation or the transfer operation in a similar manner to the first example embodiment. In FIG. 10, the transfer operation is stopped for the captured fingerprint image of the (N+6)-th frame.

Accordingly, the fingerprint image displayed on the display 214 is recorded in the HDD 208, and acquisition of a fingerprint image is stopped.

Note that, while the case where the image processing apparatus 20 performs quality determination on a fingerprint image before it is displayed on the display 214 has been described above, the timing of the quality determination by the image processing apparatus 20 is not limited thereto.

For example, the first or second example embodiment described above may be configured such that the image processing apparatus 20 determines whether or not the quality of a fingerprint image that the operator has instructed to record in the HDD 208. In this case, when the quality of the fingerprint image that the operator has instructed to record in the HDD 208 is less than a predetermined quality, the image processing apparatus 20 displays, on the display 214, an alert display notifying that the fingerprint image quality is low. Further, instead of or in addition to display of an alert indication on the display 214, the image processing apparatus 20 may sound an alert sound notifying that the fingerprint image quality is low. Such an alert indication or an alert sound can urge the operator to again acquire a fingerprint image.

Fourth Example Embodiment

A fingerprint capture system and a fingerprint capture method according to a fourth example embodiment of the present invention will be described by using FIG. 11. Note that similar elements to those in the fingerprint capture system and the fingerprint capture method according to the above-described first example embodiment are labeled with the same reference numerals, and the description thereof will be omitted or simplified.

The fingerprint capture system according to the present example embodiment is substantially similar to the fingerprint capture system according to the first example embodiment. The fingerprint capture system according to the present example embodiment displays, on the display 214, a fingerprint image captured at a time of pressing down the capture switch 160 and fingerprint images captured before and/or after the time, out of a plurality of fingerprint images repeatedly captured by the fingerprint capture device 10. The fingerprint capture system according to the present example embodiment is different in this feature from the fingerprint capture system according to the first example embodiment.

The fingerprint capture method using the fingerprint capture system according to the present example embodiment will be described below by using FIG. 11. FIG. 11 is a timing chart illustrating the operation of the fingerprint capture device and the image processing apparatus in the fingerprint capture system according to the present example embodiment. In the timing chart illustrated in FIG. 11, the horizontal axis represents time t. Further, in the timing chart illustrated in FIG. 11, among the first stage to the fifth stage arranged downward, solid-line frames in the first stage collectively represent the capture operation and transfer operation performed by the fingerprint capture device 10. Solid-line frames in the second stage represent the temporary storage operation described later of a plurality of fingerprint images performed by the image processing apparatus 20. Solid-line frames in the third stage represent the display operation performed by the image processing apparatus 20. Solid-line frames in the fourth stage represent the record operation performed by the image processing apparatus 20. Further, the numbers N provided to the solid-line frames on each stage of the first stage to the fourth stage are the same as the first example embodiment described above. Further, in the fifth stage, it is indicated that the capture switch 160 of the fingerprint capture device 10 is pressed down at the time when a signal transitions from a low level to a high level and thereby a pulse occurs.

Figure 11:
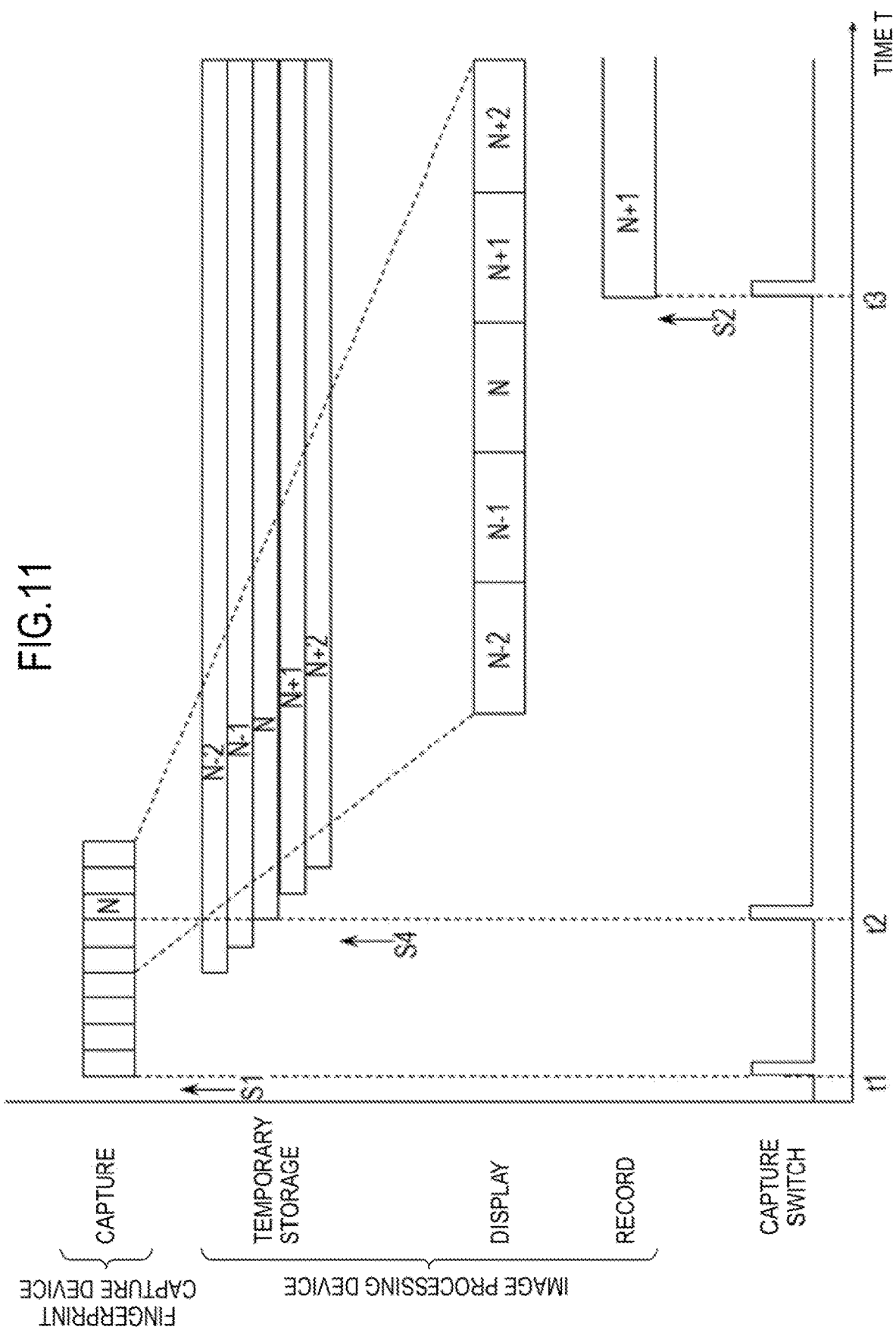
FIG. 11 is a timing chart illustrating the operation of a fingerprint capture device and an image processing apparatus of a fingerprint capture system according to a fourth example embodiment of the present invention.

As illustrated in FIG. 11, at the time t1, in response to the operator pressing down the capture switch 160 for the first time, the fingerprint capture device 10 repeats the capture operation and the transfer operation, which is the same as the first example embodiment. Note that, in the first stage of the timing chart illustrated in FIG. 11, a capture operation and a transfer operation are collectively represented as a single solid frame.

Subsequently, at the time t2, in response to the operator pressing down the capture switch 160 for the second time, a signal S4 indicating a temporary storage instruction that instructs temporary storage of a fingerprint image is input to the image processing apparatus 20. In response to the input of the signal S4 indicating a temporary storage instruction, the image processing apparatus 20 performs the temporary storage operation for the sequentially captured multiple fingerprint images. The operator is able to press down the capture switch 160 in the second time at a timing when determining it as suitable to capture a fingerprint image. For example, when an assisting person assists capturing of a fingerprint of a subject, the assisting person is able to press down the capture switch for the second time at a timing when determining that the finger of the subject is fixed at a position suitable for capturing the fingerprint.

In the temporary storage operation, the image processing apparatus 20 temporarily stores, in the RAM 206 functioning as an image memory, the sequentially captured multiple fingerprint images as fingerprint images to be displayed on the display 214. Specifically, the image processing apparatus 20 temporarily stores, in the RAM 206, a fingerprint image captured by the fingerprint capture device 10 at a time when the capture switch 160 is pressed down in the second time and fingerprint images captured before and/or after the time. In FIG. 11, a fingerprint image of the N-th frame captured at the time when the capture switch 160 is pressed down for the second time is temporarily stored. Further, two fingerprint images of the (N−2)-th frame and the (N−1)-th frame captured before the fingerprint image of the N-th frame are temporarily stored. Further, two fingerprint images of the (N+1)-th frame and the (N+2)-th frame captured after the fingerprint image of the N-th frame are temporarily stored.

Note that the fingerprint capture device 10 enters a stop state after the capture switch 160 is pressed down for the second time and the preset number of fingerprint images are captured. In FIG. 11, the fingerprint capture device 10 enters a stop state to stop the capture operation and the transfer operation after the fingerprint image of the N-th frame is captured and the two fingerprint images of the (N+1)-th frame and the (N+2)-th frame are then captured.

Subsequently, the image processing apparatus 20 performs an image processing operation and then a display operation on a plurality of fingerprint images stored in the temporary storage operation and sequentially displays these plurality of fingerprint images on the display 214. Note that the image processing operation is omitted in FIG. 11. The display time period in which the one fingerprint image is displayed on the display 214 is a time period that is longer than or equal to a capturing time period required for the fingerprint capture device 10 to capture one fingerprint image and may be a longer time period than the capturing time period, in the similar manner to the first example embodiment. Note that, instead of sequentially displaying a plurality of fingerprint images, a plurality of fingerprint images may be collectively listed as thumbnails.

The operator reviews the quality of a plurality of fingerprint images sequentially displayed on the display 214 in a similar manner to the first example embodiment and presses down the capture switch 160 when the fingerprint image displayed on the display 214 is determined to be of high quality. In FIG. 11, the fingerprint image of the (N−2)-th frame, the fingerprint image of the (N−1)-th frame, the fingerprint image of the N-th frame, the fingerprint image of the (N+1)-th frame, and the fingerprint image of the (N+2)-th frame are sequentially displayed on the display 214 with elapsing of time. At the time t3 when the fingerprint image of the (N+1)-th frame is displayed, the operator determines that the quality of the fingerprint image of the (N+1)-th frame is high and presses down the capture switch 160 for the third time.

When the operator presses down the capture switch 160 for the third time, in a similar manner to the first example embodiment, a signal S2 indicating a record instruction that instructs recording of a fingerprint image is input to the image processing apparatus 20. When the signal S2 indicating a record instruction is input, the image processing apparatus 20 records the fingerprint image displayed on the display 214 in the HDD 208 in a similar manner to the first example embodiment. In FIG. 11, the fingerprint image of the (N+1)-th frame displayed on the display 214 at the time t3 is recorded.

Note that, after the third pressing down of the capture switch 160, the image processing apparatus 20 may continue the display operation for a fingerprint image which has not yet been displayed out of the plurality of fingerprint images and subsequently give the operator opportunities of determining whether or not the fingerprint image quality is good. In this case, by the capture switch 160 being pressed down for the fourth time, the fingerprint image displayed on the display 214 is now recorded in the HDD 208. Further, instead of such a display operation, the image processing apparatus 20 may maintain a state where the fingerprint image recorded in the HDD 208 by the third pressing down of the capture switch 160 is displayed on the display 214.

Accordingly, the fingerprint image displayed on the display 214 is recorded in the HDD 208, and acquisition of a fingerprint image is stopped.

In the present example embodiment, not only a fingerprint image captured at a time when the capture switch 160 is pressed down for the second time but also fingerprint images captured before and/or after the time are displayed on the display 214. The second pressing down of the capture switch 160 can be made at a timing when the operator determines it as suitable for capturing a fingerprint image. Then, operator can review the quality of a plurality of fingerprint images displayed in such a way to determine whether or not the quality thereof is good.

Even when a fingerprint image is captured at a timing that the operator determines as suitable for capturing a fingerprint image, the quality of the fingerprint image actually captured is likely to be low. In this regard, in the present example embodiment, a fingerprint image to be recorded in the HDD 208 can be selected from a plurality of fingerprint images including not only a fingerprint image captured at a timing that the operator determines as appropriate but also fingerprint images captured before and/or after the time. Therefore, according to the present example embodiment, a higher quality fingerprint image can be acquired.

Other Example Embodiments

The image processing apparatus 20 according to the example embodiments described above can be implemented based on a computer program executed by a CPU of a computer. Such a program can be created as a program that causes a computer to execute steps for implementing respective operations and respective processes described in the example embodiments described above. A part of or a whole of the program can be provided as a computer readable storage medium recording it, such as a Digital Versatile Disc-Read Only Memory (DVD-ROM), a Compact Disc-Read Only Memory (CD-ROM), a flash memory such as a USB memory, or the like.

Figure 12:
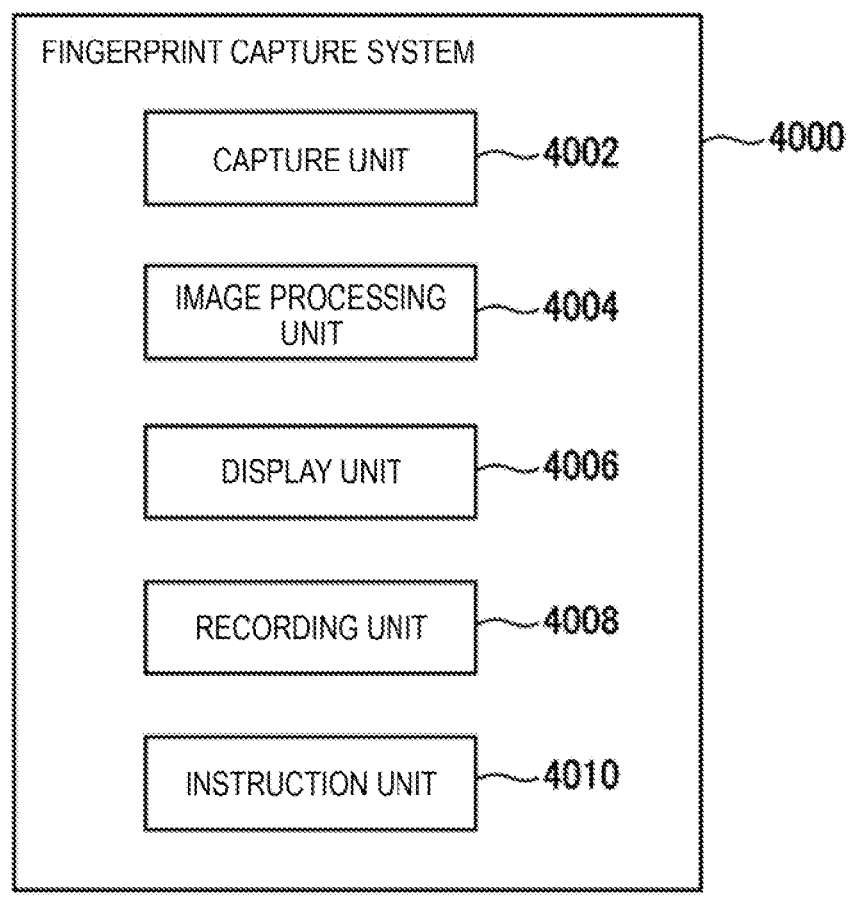
FIG. 12 is a block diagram illustrating a functional configuration of a fingerprint capture system according to another example embodiment of the present invention.

Further, the fingerprint capture system described in each of the above example embodiments can also be configured as illustrated in FIG. 12 according to another example embodiment. FIG. 12 is a block diagram illustrating a functional configuration of a fingerprint capture system according to another example embodiment.

As illustrated in FIG. 12, a fingerprint capture system 4000 according to another example embodiment has a capture unit 4002 that captures a fingerprint and an image processing unit 4004 to which a fingerprint image of the fingerprint captured by the capture unit 4002 is transferred and that processes the fingerprint image. Further, the fingerprint capture system 4000 has a display unit 4006 on which the fingerprint image transferred to the image processing unit 4004 is displayed and a recording unit 4008 in which the fingerprint image transferred to the image processing unit 4004 is recorded by the image processing unit 4004. Furthermore, the fingerprint capture system 4000 has an instruction unit 4010 that inputs, in the image processing unit 4004, a record instruction that instructs the image processing unit 4004 to record the fingerprint image in the recording unit 4008. The image processing unit 4004 records, in the recording unit 4008, the fingerprint image displayed on the display unit 4006 at the time when the record instruction is input by the instruction unit 4010.

According to the fingerprint capture system 4000 of another example embodiment, a high quality fingerprint image can be acquired.

Figure 13:
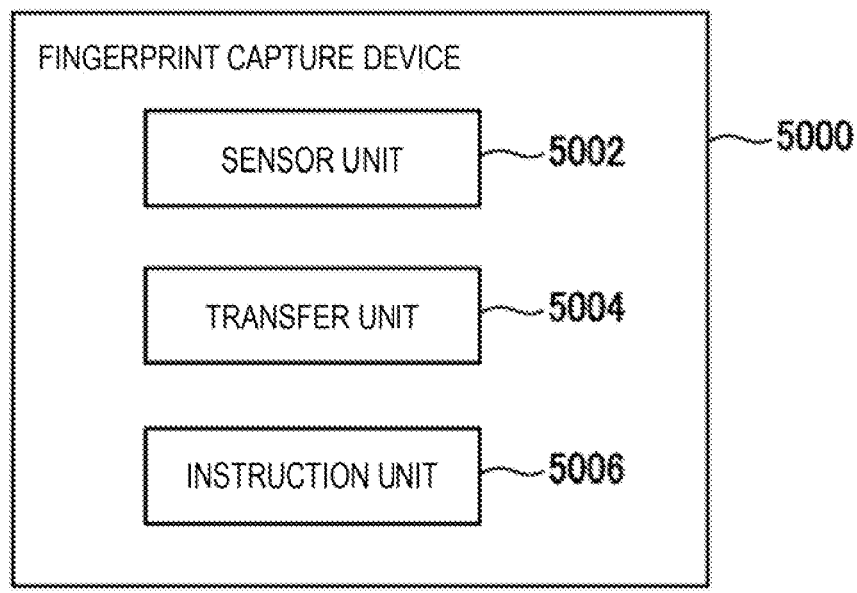
FIG. 13 is a block diagram illustrating a functional configuration of a fingerprint capture device according to another example embodiment of the present invention.

Further, the fingerprint capture device described in each of the above example embodiments can also be configured as illustrated in FIG. 13 according to another example embodiment. FIG. 13 a block diagram illustrating a functional configuration of a fingerprint capture device according to another example embodiment.

As illustrated in FIG. 13, a fingerprint capture device 5000 according to another example embodiment has a sensor unit 5002 that captures a fingerprint and a transfer unit 5004 that transfers a fingerprint image to an image processing unit in order to display a fingerprint image of a fingerprint captured by the sensor unit 5002 on a display unit. Further, the fingerprint capture device 5000 has an instruction unit 5006 that inputs, to the image processing unit, a record instruction that instructs recording of a fingerprint image transferred to the image processing unit and displayed on the display unit into a recording unit.

According to the fingerprint capture device 5000 of another example embodiment, a high quality fingerprint image can be acquired.

Figure 14:
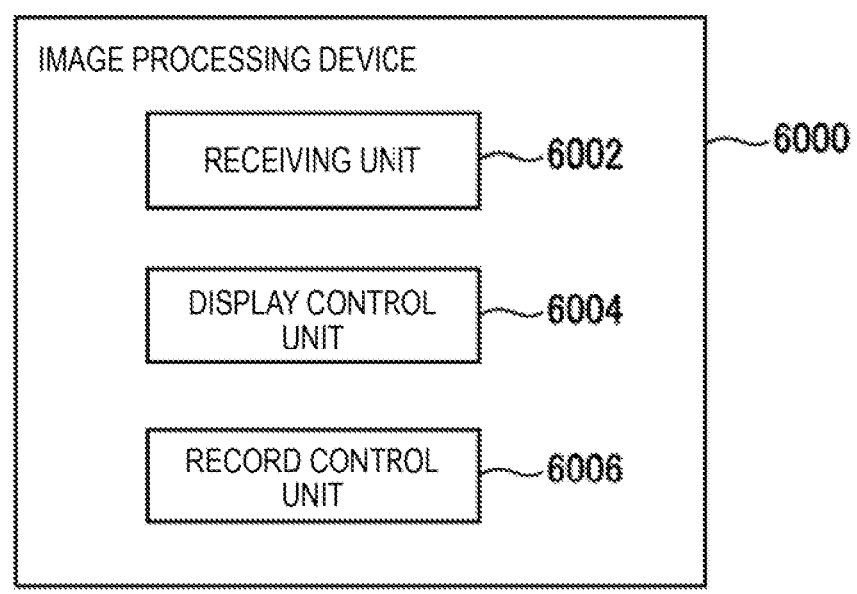
FIG. 14 is a block diagram illustrating a functional configuration of an image processing apparatus according to another example embodiment of the present invention.

Further, the image processing apparatus described in each of the above example embodiments can also be configured as illustrated in FIG. 14 according to another example embodiment. FIG. 14 a block diagram illustrating a functional configuration of an image processing apparatus according to another example embodiment.

As illustrated in FIG. 14, an image processing apparatus 6000 according to another example embodiment has a receiving unit 6002 that receives a fingerprint image of a fingerprint captured by a capture unit that captures a fingerprint and a display control unit 6004 that displays the fingerprint image received by the receiving unit 6002 on a display unit. Furthermore, the image processing apparatus 600 has a record control unit 6006 that records the fingerprint image in a recording unit based on a record instruction that instructs recording of the fingerprint image displayed on the display unit in the recording unit.

According to the image processing apparatus 6000 of another example embodiment, a high quality fingerprint image can be acquired.

Modified Example Embodiments

Further, the present invention is not limited to the example embodiments described above, and various modifications are possible.

For example, while the case where the fingerprint capture device 10 captures a fingerprint by utilizing a near-infrared light has been described as an example in the above example embodiments, the fingerprint capture device 10 is not necessarily limited to those utilize a near-infrared light as long as the fingerprint capture device captures a fingerprint.

Further, while the case where the fingerprint capture device 10 acquires a fingerprint of a single finger has been described as an example in the above example embodiments, it is possible to capture fingerprint images of a plurality of fingers at the same time.

Further, while the case where the capture switch 160 is provided on the bottom face of the holding portion 1102 of the casing 110 has been described as an example in the above example embodiments, the position where the capture switch 160 is provided is not limited thereto. For example, the capture switch 160 may be provided on the side face of the holding unit 1102.

The part or whole of the example embodiments disclosed above can be described as, but not limited to, the following supplementary notes.

(Supplementary Note 1)

A fingerprint capture system comprising:

a capture unit that captures a fingerprint;

an image processing unit to which a fingerprint image of the fingerprint captured by the capture unit is transferred and that processes the fingerprint image;

a display unit on which the fingerprint image transferred to the image processing unit is displayed;

a recording unit in which the fingerprint image transferred to the image processing unit is recorded by the image processing unit; and an instruction unit that inputs, in the image processing unit, a record instruction that instructs the image processing unit to record the fingerprint image in the recording unit, wherein the image processing unit records, in the recording unit, the fingerprint image displayed on the display unit at a time when the record instruction is input by the instruction unit.

(Supplementary Note 2)

The fingerprint capture system according to supplementary note 1, wherein the capture unit sequentially captures a plurality of fingerprint images for a same finger, and wherein the plurality of fingerprint images are sequentially displayed on the display unit each for a display time period that is longer than or equal to a capturing time period required for the capture unit to capture each one of the fingerprint images.

(Supplementary Note 3)

The fingerprint capture system according to supplementary note 2, wherein the plurality of fingerprint images are reduced at a constant time interval and sequentially displayed on the display unit.

(Supplementary Note 4)

The fingerprint capture system according to any one of supplementary notes 1 to 3, wherein the image processing unit determines whether or not a quality of the fingerprint image that the instruction unit has instructed to record in the recording unit is good.

(Supplementary Note 5)

The fingerprint capture system according to supplementary note 1, wherein the capture unit sequentially captures a plurality of fingerprint images for a same finger, wherein the image processing unit determines whether or not each quality of the plurality of fingerprint images is good, and wherein, out of the plurality of fingerprint images on which whether or not a quality is good has been determined by the image processing unit, the fingerprint images above a predetermined quality are sequentially displayed on the display unit.

(Supplementary Note 6)

The fingerprint capture system according to supplementary note 1, wherein the capture unit sequentially captures a plurality of fingerprint images for a same finger, wherein, before the record instruction, the instruction unit inputs, to the image processing unit, a temporary storage instruction that instructs the image processing unit to temporarily store the fingerprint image, wherein the image processing unit temporarily stores the fingerprint image captured by the capture unit at a time when the temporary storage instruction is input and the fingerprint images captured before and/or after the time, and wherein the plurality of fingerprint images temporarily stored by the image processing unit are displayed on the display unit.

(Supplementary Note 7)

The fingerprint capture system according to any one of supplementary notes 1 to 5, wherein the instruction unit inputs the record instruction and inputs, to the capture unit, a stop instruction that instructs the capture unit to stop.

(Supplementary Note 8)

The fingerprint capture system according to any one of supplementary notes 1 to 7, wherein the instruction unit is provided in the capture unit.

(Supplementary Note 9)

A fingerprint capture device comprising:

a sensor unit that captures a fingerprint;

a transfer unit that, in order to display a fingerprint image of the fingerprint captured by the sensor unit on a display unit, transfers the fingerprint image to an image processing unit; and an instruction unit that inputs, into the image processing unit, a record instruction that instructs recording of the fingerprint image transferred to the image processing unit and displayed on the display unit into a recording unit.

(Supplementary Note 10)

An image processing apparatus comprising:

a receiving unit that receives a fingerprint image of a fingerprint captured by a capture unit that captures the fingerprint;

a display control unit that displays the fingerprint image received by the receiving unit on a display unit; and a recording control unit that, based on a record instruction that instructs recording of the fingerprint image displayed on the display unit in a recording unit, records the fingerprint image in the recording unit.

(Supplementary Note 11)

A fingerprint capture method comprising:

capturing a fingerprint;

transferring a fingerprint image of the captured fingerprint;

displaying the transferred fingerprint image;

recording the transferred fingerprint image; and inputting a record instruction that instructs recording of the fingerprint image, wherein the recording of the fingerprint image records the fingerprint image displayed at a time when the record instruction is input.

(Supplementary Note 12)

A storage medium in which a program is stored, the program causing a computer that processes a fingerprint image transferred from a fingerprint capture device that captures a fingerprint to execute:

displaying a fingerprint image transferred from the fingerprint capture device; and recording the fingerprint image transferred from the fingerprint capture device, wherein the recording records the fingerprint image displayed at a time when a record instruction that instructs recording of the fingerprint image is input.

While the present invention has been described above with reference to the example embodiments, the present invention is not limited to the example embodiments described above. Various changes that can be appreciated by those skilled in the art within the scope of the present invention may be applied to the configuration or the detail of the present invention.

Further, the whole content of Japanese Patent No. 3751872 is quoted to be a part of this application.

REFERENCE SIGNS LIST 1 fingerprint capture system
10 fingerprint capture device
130 two-dimensional image sensor
160 capture switch
20 image processing apparatus
214 display

The invention claimed is:

1. A system comprising:
  a scanner capturing a biometrics information of a child, the scanner comprising a holding portion that can be held with one hand of a person and the scanner sequentially capturing fingerprint images of a same finger or toe print images of a same toe;
  a capture switch provided in the holding portion, wherein the capture switch can be pushed while the holding portion is held by the one hand; and
  at least one processor configured to run a computer program to perform:
  outputting, to a display, a first guide information indicating a first object that is a part of the child to be captured by the scanner,
  sequentially outputting, to the display, the biometrics information of the child captured by the scanner,
  recording the biometrics information of the child output to the display, in response to the capture switch being pushed,
  determining whether or not each quality of the fingerprint images or the toe print images is above a predetermined quality, and
  displaying the fingerprint images or the toe print images above the predetermined quality on the display sequentially.

2. The system according to claim 1, wherein the at least one processor is further configured to perform:
  outputting, to the display, a second guide information indicating a second object that is a part of the child after said recording, the second object is different from the first object.

3. The system according to claim 1, wherein the at least one processor is further configured to perform:
  outputting, to the display, together with a preview window displaying a preview of a biometrics image transferred from the scanner, at least one of (i) an ID entry area to which an ID of the child who is captured is input, (ii)

a name entry area to which the name of the child is input, and (iii) a biometrics type area displaying a type of the one biometrics image displayed.

4. The system according to claim 1, further comprising the scanner configured to capture the biometrics information as a fingerprint of a child's finger or a toe print of a child's toe.

5. A method by a system comprising a scanner, capturing a biometrics information of a child and the scanner sequentially capturing fingerprint images of a same finger or toe print images of a same toe, and the scanner comprising a holding portion that can be held with one hand of a person, a capture switch, provided in the holding portion, the capture switch can be pushed with the one hand while the holding portion is held by the one hand, and at least one processor, the method comprising:
outputting, to a display, a first guide information indicating a first object that is a part of the child to be captured by the scanner,
sequentially outputting, to the display, the biometrics information of the child captured by the scanner,
recording the biometrics information of the child output to the display, in response to the capture switch being pushed,
determining whether or not each quality of the fingerprint images or the toe print images is above a predetermined quality, and
displaying the fingerprint images or the toe print images above the predetermined quality on the display sequentially.

6. The method according to claim 5, comprising:
outputting, to the display, a second guide information indicating a second object that is a part of the child after said recording, the second object is different from the first object.

7. The method according to claim 5, comprising:
outputting, to the display, together with a preview window displaying a preview of a biometrics image transferred from the scanner, at least one of (i) an ID entry area to which an ID of the child who is captured is input, (ii) a name entry area to which the name of the child is input, and (iii) a biometrics type area displaying a type of the one biometrics image displayed.

8. The method according to claim 5, the system further comprising the scanner configured to capture the biometrics information as a fingerprint of a child's finger or a toe print of a child's toe.

* * * * *